(12) United States Patent
Peck et al.

(10) Patent No.: US 9,803,239 B2
(45) Date of Patent: Oct. 31, 2017

(54) FLOW CELLS FOR HIGH DENSITY ARRAY CHIPS

(71) Applicant: Complete Genomics, Inc., Mountain View, CA (US)

(72) Inventors: Bill J. Peck, Mountain View, CA (US); Mark Fuller, Mountain View, CA (US); Daniel West, Mountain View, CA (US); Anthony Delacruz, Mountain View, CA (US)

(73) Assignee: Complete Genomics, Inc., San Jose, CA (US)

( * ) Notice: Subject to any disclaimer, the term of this patent is extended or adjusted under 35 U.S.C. 154(b) by 0 days.

(21) Appl. No.: 13/840,482

(22) Filed: Mar. 15, 2013

(65) Prior Publication Data

US 2013/0281305 A1   Oct. 24, 2013

Related U.S. Application Data

(60) Provisional application No. 61/617,628, filed on Mar. 29, 2012.

(51) Int. Cl.
    *B01L 3/00* (2006.01)
    *C12Q 1/68* (2006.01)
    *G01N 21/05* (2006.01)

(52) U.S. Cl.
    CPC ...... *C12Q 1/6874* (2013.01); *B01L 3/502715* (2013.01); *B01L 3/502723* (2013.01);
    (Continued)

(58) Field of Classification Search
    CPC ....... B01L 2200/027; B01L 2200/0684; B01L 2300/0636; B01L 2300/0816;
    (Continued)

(56) References Cited

U.S. PATENT DOCUMENTS 2,942,520 A   6/1960  George
4,683,195 A   7/1987  Mullis et al.
(Continued)

FOREIGN PATENT DOCUMENTS

AU   2013204253 A1   1/2017
CN   1265049         8/2000
(Continued)

OTHER PUBLICATIONS

International Search Report and Written Opinion for PCT Patent Application No. PCT/US2013/33583 dated Jun. 10, 2013, 9 pages.
(Continued)

*Primary Examiner* — Jennifer Wecker
(74) *Attorney, Agent, or Firm* — Kilpatrick Townsend & Stockton LLP

(57) ABSTRACT

Biochemical flow cells having sealed inlets and outlets are provided for performing high-volume assays on macromolecules. In one example embodiment, a flow cell with detachable inlet and outlet connectors comprises an inlet manifold, a coverslip, and a substrate disposed below the coverslip to form a reaction chamber, where the substrate is disposed to partially cover the inlet manifold such that a slit is formed along an entire edge of the substrate where fluids can flow from the inlet manifold through the slit, around substantially the entire edge of the substrate, and into the reaction chamber at equalized pressure and without bubbles. In another embodiment, a flow cell comprises an outlet manifold, two or more flow regions each connected to its own loading port via its own flow distribution funnel, each loading port connected to the outlet manifold, and plugs in a wall of the outlet manifold opposite each loading port, such that when a plug is absent from the wall of the outlet manifold, a loading tip may be inserted in its place, passing (Continued)

through the outlet manifold and connecting directly to a loading port.

15 Claims, 13 Drawing Sheets

(52) U.S. Cl.
CPC ......... *B01L 3/565* (2013.01); *B01L 2200/027* (2013.01); *B01L 2200/0684* (2013.01); *B01L 2300/0636* (2013.01); *B01L 2300/0816* (2013.01); *B01L 2300/0819* (2013.01); *B01L 2300/0822* (2013.01); *B01L 2300/0877* (2013.01); *G01N 21/05* (2013.01)

(58) Field of Classification Search
CPC ..... B01L 2300/0819; B01L 2300/0822; B01L 2300/0877; B01L 3/502715; B01L 3/502723; B01L 3/565; C12Q 1/6874; G01N 21/05
See application file for complete search history.

(56) References Cited

U.S. PATENT DOCUMENTS

| | | | |
|---|---|---|---|
| 4,683,202 A | 7/1987 | Mullis | |
| 4,800,159 A | 1/1989 | Mullis et al. | |
| 4,965,188 A | 10/1990 | Mullis et al. | |
| 5,122,345 A | 6/1992 | Tabor et al. | |
| 5,210,015 A | 5/1993 | Gelfand et al. | |
| 5,288,468 A | 2/1994 | Church et al. | |
| 5,399,491 A | 3/1995 | Kacian et al. | |
| 5,854,033 A | 12/1998 | Lizardi | |
| 5,958,760 A | 9/1999 | Freeman | |
| 6,174,670 B1 | 1/2001 | Wittwer et al. | |
| 6,210,891 B1 | 4/2001 | Nyren et al. | |
| 6,287,824 B1 | 9/2001 | Lizardi | |
| 6,309,824 B1 | 10/2001 | Drmanac | |
| 6,326,489 B1 | 12/2001 | Church et al. | |
| 6,396,995 B1 | 5/2002 | Stuelpnagel et al. | |
| 6,401,267 B1 | 6/2002 | Drmanac | |
| 6,403,320 B1 | 6/2002 | Read et al. | |
| 6,432,360 B1 | 8/2002 | Church | |
| 6,485,944 B1 | 11/2002 | Church et al. | |
| 6,510,007 B1 | 1/2003 | Blasenheim | |
| 6,511,803 B1 | 1/2003 | Church et al. | |
| 6,544,732 B1 | 4/2003 | Chee et al. | |
| 6,548,021 B1 | 4/2003 | Church et al. | |
| 6,551,554 B1 | 4/2003 | Vermeiden et al. | |
| 6,611,634 B2 | 8/2003 | Herron et al. | |
| 6,670,170 B1 | 12/2003 | Gaffin et al. | |
| 6,787,308 B2 | 9/2004 | Balasubramanian et al. | |
| 6,828,100 B1 | 12/2004 | Ronaghi | |
| 6,833,246 B2 | 12/2004 | Balasubramanian | |
| 6,864,052 B1 | 3/2005 | Drmanac et al. | |
| 6,911,345 B2 | 6/2005 | Quake et al. | |
| 6,960,437 B2 | 11/2005 | Enzelberger et al. | |
| 7,022,515 B2 | 4/2006 | Herron et al. | |
| 7,070,927 B2 | 7/2006 | Drmanac | |
| 7,115,400 B1 | 10/2006 | Adessi et al. | |
| 7,118,910 B2 | 10/2006 | Unger et al. | |
| 7,170,050 B2 | 1/2007 | Turner et al. | |
| 7,220,549 B2 | 5/2007 | Buzby | |
| 7,232,656 B2 | 6/2007 | Balasubramanian et al. | |
| 7,244,559 B2 | 7/2007 | Rothberg et al. | |
| 7,264,929 B2 | 9/2007 | Rothberg et al. | |
| 7,278,210 B2 | 10/2007 | Howitz et al. | |
| 7,302,146 B2 | 11/2007 | Turner et al. | |
| 7,678,565 B2 | 3/2010 | Schurmann-Mader et al. | |
| 7,854,892 B2 | 12/2010 | Veiner et al. | |
| 8,298,768 B2 | 10/2012 | Drmanac et al. | |
| 8,445,194 B2 | 5/2013 | Drmanac et al. | |
| 2002/0039797 A1 | 4/2002 | Bonde et al. | |
| 2003/0107731 A1 | 6/2003 | De Kock et al. | |
| 2004/0137604 A1 | 7/2004 | Goodman et al. | |
| 2004/0141880 A1 | 7/2004 | Handler et al. | |
| 2005/0191656 A1 | 9/2005 | Drmanac | |
| 2005/0196320 A1 | 9/2005 | Veiner | |
| 2005/0244863 A1 | 11/2005 | Mir | |
| 2005/0271560 A1 | 12/2005 | Rodgers | |
| 2006/0024711 A1 | 2/2006 | Lapidus et al. | |
| 2006/0182664 A1* | 8/2006 | Peck ................ B01J 19/0046 422/400 |
| 2007/0054299 A1 | 3/2007 | Heller et al. | |
| 2007/0087362 A1 | 4/2007 | Church et al. | |
| 2007/0128610 A1 | 6/2007 | Buzby | |
| 2007/0172993 A1 | 7/2007 | Peck et al. | |
| 2007/0207482 A1 | 9/2007 | Church et al. | |
| 2007/0264675 A1 | 11/2007 | Toner et al. | |
| 2009/0035770 A1 | 2/2009 | Mathies et al. | |
| 2009/0155793 A1 | 6/2009 | Oliphant | |
| 2009/0264299 A1 | 10/2009 | Drmanac et al. | |
| 2010/0129789 A1 | 5/2010 | Self et al. | |
| 2010/0205139 A1 | 8/2010 | Xia et al. | |
| 2011/0071053 A1 | 3/2011 | Drmanac et al. | |
| 2011/0201099 A1* | 8/2011 | Anderson .............. G01N 21/05 435/287.2 |
| 2012/0004139 A1 | 1/2012 | Staker | |
| 2012/0004140 A1 | 1/2012 | Staker | |

FOREIGN PATENT DOCUMENTS

| | | |
|---|---|---|
| DE | 10 2006 038271 A1 | 2/2008 |
| WO | 99/19341 A1 | 4/1999 |
| WO | 01/35088 A1 | 5/2001 |
| WO | 02/103331 A1 | 12/2002 |
| WO | 2004/029221 A2 | 4/2004 |
| WO | 2005/082098 A2 | 9/2005 |
| WO | 2006/073504 A2 | 7/2006 |
| WO | 2007/019479 A2 | 2/2007 |
| WO | 2013/148525 A1 | 10/2013 |

OTHER PUBLICATIONS

International Preliminary Report on Patentability for PCT Patent Application No. PCT/ US2013/33583 dated Oct. 1, 2014, 5 pages.
Allawi et al., "Thermodynamics and NMR of Internal G•T Mismatches in DNA," Biochemistry 1997, 36:10581-94.
Cheek et al., Chemiluminescence Detection for Hybridization Assays on the Flow-Thru Chip, a Three Dimensional Microchannel Biochip. Analytical Chemistry (Dec. 15, 2001); 73(24): 5777-5783.
Kessler et al., Use of DNA Flow-Thru Chip, a Three-Dimensional Biochip, for Typing and Subtyping of Influenza Viruses. Journal of Clinical Microbiology (May 2004); 42(5): 2173-2185.
Li et al., "A photocleavable fluorescent nucleotide for DNA sequencing and analysis," Proc. Natl. Acad. Sci., Jan. 21, 2003, 100:414-419.
Ronaghi et al., "A Sequencing Method Baseed on Real-Time Pyrophosphate," Science, Jul. 17, 1998, 281:363-365.
Shendure et al., "Accurate Multiplex Polony Sequencing of an Evolved Bacterial Genome," Science, 2005, 309:1728-1739.
Chinese Office Action issued in CN Application No. CN 201380026167.9 dated Aug. 4, 2016, 7 pages.
Australian Application No. 2013204253, First Examiner Report dated Dec. 17, 2014, 3 pages.
Chinese Application No. 201380026167.9, Office Action dated Aug. 26, 2015, 20 pages (8 pages for the original document and 12 pages for the English translation).
Chinese Application No. 201380026167.9, Office Action dated Apr. 20, 2016, 7 pages (3 pages for the original document and 4 pages for the English translation).
Extended European Search Report for European Patent Application No. 13767823 dated Oct. 21, 2015, 10 pages.
Chinese Application No. 201380026167.9, Notification of the Decision to Grant a Patent Right for Patent for Invention, dated Jan. 12, 2017, 3 pages (2 pages of translation).

* cited by examiner

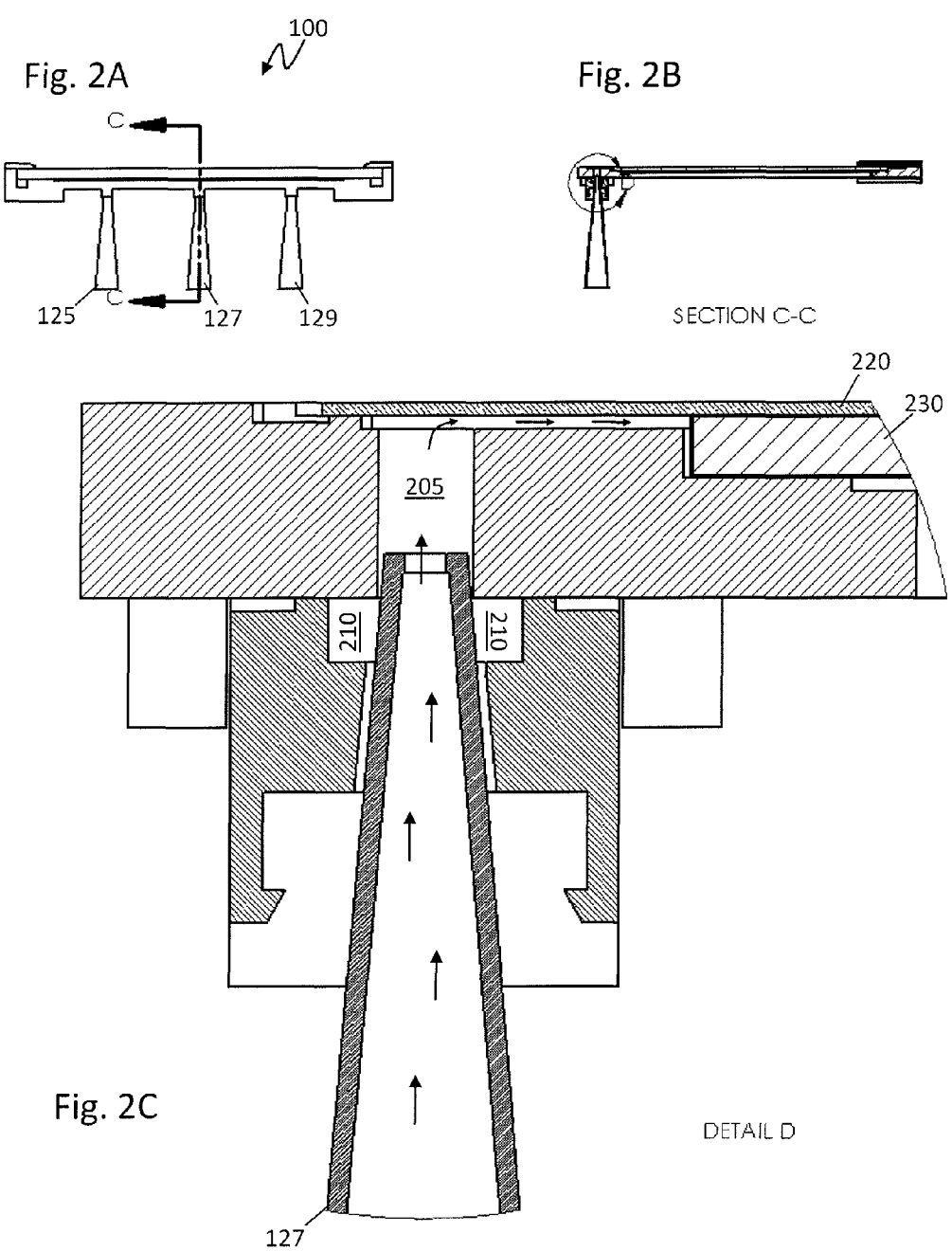

Fig. 3A
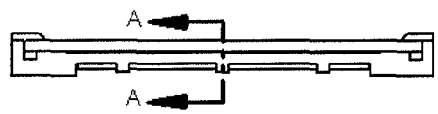
Fig. 3B
SECTION A-A
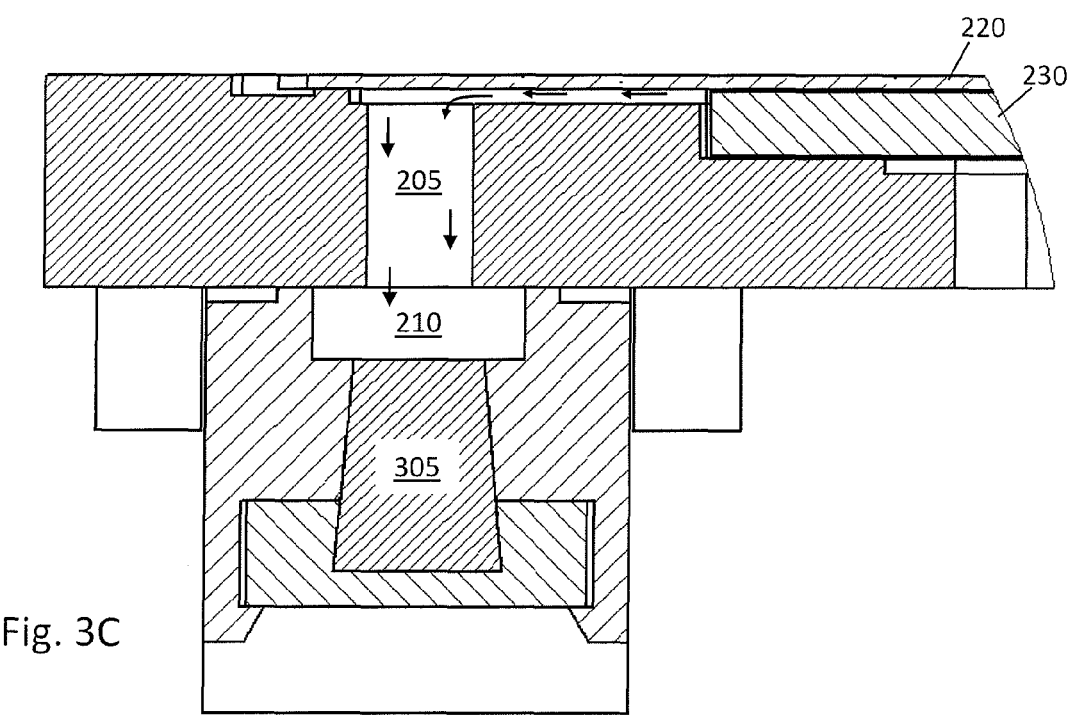
Fig. 3C
DETAIL B

SECTION E-E

SECTION F-F
(inlet manifold side)

SECTION G-G
(outlet manifold side)

(seal seated against flow cell)

FLOW CELLS FOR HIGH DENSITY ARRAY CHIPS

CROSS-REFERENCES TO RELATED APPLICATIONS

This application claims benefit under 35 U.S.C. §119(a) to provisional patent application Ser. No. 61/627,628 filed Mar. 29, 2012.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This invention relates to devices used in biochemical diagnostic tools and particularly to devices suited to receive and expel fluids and containing biochemical array chips that are configured to perform assays.

Selected Definitions

As used herein and in the appended claims, the singular forms "a," "an," and "the" may include plural referents unless the context clearly dictates otherwise. Thus, for example, reference to "an attachment site", unless the context dictates otherwise, may refer to multiple such attachment sites, and reference to "a method for sequence determination" may include reference to equivalent steps and methods that may be used by those skilled in the art, and so forth.

Unless defined otherwise, all technical and scientific terms used herein have the same meaning as commonly understood by one of ordinary skill in the art to which this invention belongs.

Where a range of values is provided, it is understood that each intervening value, between the upper and lower limit of that range and any other stated or intervening value or sub-range in that stated range is encompassed within the invention. The upper and lower limits of such smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Various embodiments of the flow cells described herein may use reagents, buffers, and other fluids that are prepared by conventional techniques involving organic chemistry, polymer technology, molecular biology (including recombinant techniques), cell biology, and biochemistry, which are within the skill of those who practice in the art. Such conventional techniques may include, without limitation, polymer array synthesis, hybridization, and ligation of polynucleotides, and detection of hybridization using a label. Specific illustrations of suitable techniques can be had by reference to the examples herein. However, other equivalent procedures can, of course, also be used.

"Amplicon" refers to the product of a polynucleotide amplification reaction. For example, an amplicon may be a population of polynucleotides that are replicated from one or more starting sequences. Amplicons may be produced by a variety of amplification reactions, including but not limited to polymerase chain reactions (PCRs), linear polymerase reactions, nucleic acid sequence-based amplification, circle dependent amplification and like reactions.

"Array" refers to a solid phase support (e.g., such as a substrate) having a surface, preferably but not exclusively a planar or substantially planar surface, which carries an array of attachment sites to which nucleic acids or macromolecules have attached, such that an attachment site of the array comprises oligonucleotides or polynucleotides and is spatially defined and not overlapping with other member sites of the array; that is, the sites are spatially discrete. The array can also comprise a non-planar structure with a surface such as a bead or a well. The oligonucleotides or polynucleotides of the array may be covalently bound to the solid support, or may be non-covalently bound. As may be used herein, "random array" or "random microarray" refers to a microarray where the identity of the oligonucleotides or polynucleotides is not discernable, at least initially, from their location but may be determined by a particular operation on the array, such as by sequencing, hybridizing decoding probes, or the like.

"Complementary" or "substantially complementary" refers to the hybridization or base pairing or the formation of a duplex between nucleotides or nucleic acids, such as, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%.

"Duplex" means at least two oligonucleotides or polynucleotides that are fully or partially complementary and which undergo Watson-Crick type base pairing among all or most of their nucleotides so that a stable complex is formed. The terms "annealing" and "hybridization" are used interchangeably to mean formation of a stable duplex. "Perfectly matched" in reference to a duplex means that the poly-or oligonucleotide strands making up the duplex form a double-stranded structure with one another such that every nucleotide in each strand undergoes Watson-Crick base pairing with a nucleotide in the other strand. A "mismatch" in a duplex between two oligonucleotides or polynucleotides means that a pair of nucleotides in the duplex fails to undergo Watson-Crick base pairing.

"Hybridization" refers to the process in which two single-stranded polynucleotides bind non-covalently to form a stable double-stranded polynucleotide. The resulting (and usually) double-stranded polynucleotide is a "hybrid" or "duplex." "Hybridization conditions" will typically include salt concentrations of less than about 1M, more typically less than about 500 mM and may be less than about 200 mM. A "hybridization buffer" is a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, e.g., conditions under which a probe will hybridize to its target subsequence but will not hybridize to the other, uncomplimentary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. Exemplary stringent conditions include a salt concentration of at least 0.01M to no more than 1M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of 30° C. are suitable for allele-specific probe hybridizations.

"Ligation" refers to the process of forming a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide "Macromolecule" used in relation to a nucleic acid means a nucleic acid having a measurable three dimensional structure, including linear nucleic acid molecules with comprising secondary structures (e.g., amplicons), branched nucleic acid molecules, and multiple separate copies of individual with interacting structural elements, e.g., complementary sequences, palindromes, or other sequence inserts that cause three-dimensional structural elements in the nucleic acid.

"Nucleic acid", "oligonucleotide", "polynucleotide", "oligo" or grammatical equivalents used herein refers generally to at least two nucleotides covalently linked together. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, nonionic backbones, and non-ribose backbones. Modifications of the ribose-phosphate backbone may be done to increase the stability of the molecules; for example, PNA:DNA hybrids can exhibit higher stability in some environments. For a nucleic acid, a polynucleotide fragment, or a library construct to be "derived" from a biological sample can mean that the nucleic acid, polynucleotide fragment, or library construct is formed by physically, chemically, and/or enzymatically fragmenting one or more polynucleotides from the biological sample. To be "derived" from a polynucleotide may also mean that the nucleic acid, polynucleotide fragment, or library construct is the result of a replication or amplification of a particular subset of the nucleotides in the source polynucleotide.

"Primer" refers to an oligonucleotide, either natural or synthetic, which is capable, upon forming a duplex with a polynucleotide template, of acting as a point of initiation of nucleic acid synthesis and being extended from one of its ends along the template so that an extended duplex is formed. The sequence of nucleotides added during the extension process is determined by the sequence of the template polynucleotide. Primers usually are extended by a DNA polymerase.

"Probe" means generally an oligonucleotide that is complementary to an oligonucleotide or target nucleic acid under investigation. Preferably, probes used in certain embodiments are labeled in a way that permits detection, e.g., with a fluorescent or other optically-discernible tag.

"Sequence determination" (also referred to as "sequencing") in reference to a target nucleic acid means determination of information relating to the sequence of nucleotides in the target nucleic acid. Such information may include the identification or determination of partial and/or full sequence information of the target nucleic acid. The sequence information may be determined with varying degrees of statistical reliability or confidence. In one aspect, the term "sequencing" includes the determination of the identity and ordering of a plurality of contiguous nucleotides in a target nucleic acid starting from different nucleotides in the target nucleic acid.

"Target nucleic acid" means a nucleic acid from a gene, a regulatory element, genomic DNA, cDNA, RNAs (including mRNAs, rRNAs, siRNAs, miRNAs, and the like), and fragments thereof. A target nucleic acid may be a nucleic acid from a sample, or a secondary nucleic acid such as a product of an amplification reaction.

As used herein, the term "$T_m$" is commonly defined as the temperature at which half of the population of double-stranded nucleic acid molecules becomes dissociated into single strands. The equation for calculating the $T_m$ of nucleic acids is well known in the art. As indicated by standard references, a simple estimate of the $T_m$ value may be calculated by the equation: $T_m=81.5+16.6(\log 10[Na+])0.41 (\%[G+C])-675/n-1.0$ m, when a nucleic acid is in aqueous solution having cation concentrations of 0.5 M, or less, the (G+C) content is between 30% and 70%, n is the number of bases, and m is the percentage of base pair mismatches.

History of Biochemical Array Chips

Biochemical array chips allow millions of biochemical experiments to be performed in parallel. This ability accrues from the development of techniques to perform each experiment in a very small volume and to pack the experiments very close together on an array chip. Array chips have solid (and usually planar) substrates made from silicon or glass wafers, or other materials. Biomolecules, reagents, fluorescent markers and other chemical compounds may be applied to array chips in regular patterns.

Two types of structures for applying reagents and buffers to a biochemical array chip are flow slides and flow cells. A flow slide holds an array chip as liquids are washed over it. The flow slide is open to the environment. In deoxyribonucleic acid (DNA) sequencing, flow slides may suffer from inadequate control of various parameters (e.g., such as dosage, concentration, time, temperature, etc.), are prone to bubbles forming in solution, and do little to prevent evaporation. The rate of flow of liquids across a flow slide is determined mainly by gravity, and substantial "fingers" of Saffman-Taylor instability can develop when low viscosity wash buffers are introduced after higher viscosity reagents.

The following patent applications provide additional information on various assays that may be used in conjunction with the flow cells and flow cell components described herein: U.S. patent application Ser. No. 11/451,691 filed on Jun. 13, 2006; Ser. No. 11/679,124 filed on Feb. 24, 2007; Ser. No. 12/325,922 filed on Dec. 1, 2008; and in various systems such as those described in U.S. patent application Ser. No. 12/261,548 filed on Oct. 30, 2008.

In contrast to flow slides, a flow cell is a device that encloses a biochemical array chip (e.g., under a coverslip). In operation, a flow cell is closed to the environment and offers a closed liquid path that prevents evaporation.

Currently available flow cells suffer from some disadvantages. For example, in current flow cells some of the area of the array chips is lost because of various artificial restrictors (e.g., such as holes, channels, etc., in and/or on the chip) that are used to dispense fluids on to the chips' surface. In addition, such artificial restrictors do not naturally allow for substantially uniform dispensing of fluids across an array chip, which subjects the experiments conducted on the chip's surface to non-uniform conditions. Moreover, because of the closed-system nature of a flow cell, fluids are dispensed to a typical currently-available flow cell through fluid connections (e.g., tubes, pumps, valves, etc.) that are permanently attached to the flow cell. The use of such permanent fluid connections, however, restricts how various operations (e.g., such as operations performed in DNA sequencing) can be performed on the experiments conducted in the flow cell.

SUMMARY

According to the invention, biochemical flow cells having sealed inlets and outlets are provided for performing high-volume assays on macromolecules. In one embodiment, a flow cell with detachable inlet and outlet connectors comprises an inlet manifold, a coverslip, and a substrate disposed below the coverslip to form a reaction chamber, where the substrate is disposed to partially cover the inlet manifold such that a slit is formed along an entire edge of the substrate from which fluids from the inlet manifold can flow through the slit, around substantially the entire edge of the substrate, and into the reaction chamber, thus uniformly filling the reaction chamber, wherein the slit creates a manifolding effect such that the fluid pressure is substantially equal along the entire length of the slit. This substantial pressure equalization is maintained by the reaction chamber itself, which acts as a manifold for the fluid that enters it through the slit. In addition, undesired bubbles are kept from the reaction chamber.

In another embodiment, a flow cell comprises an outlet manifold, two or more flow regions each connected to its own loading port via its own flow distribution funnel, each loading port connected to the outlet manifold, and plugs in a wall of the outlet manifold opposite each loading port, such that when a plug is absent from the wall of the outlet manifold, a loading tip may be inserted in its place, passing through the outlet manifold and connecting directly to a loading port.

Further according to the invention, methods of utilization of flow cells are provided to take advantage of the features of the flow cells.

The invention will be better understood by reference to the following detailed description in connection with the accompanying drawings.

BRIEF DESCRIPTION OF THE DRAWINGS

FIGS. 2A, 2B and 2C illustrate details of the outlet manifold of the flow cell of FIG. 1 during loading.

FIGS. 3A, 3B and 3C illustrate details of the outlet manifold of the flow cell of FIG. 1 when it is plugged.

DETAILED DESCRIPTION OF THE INVENTION

Figure 1:
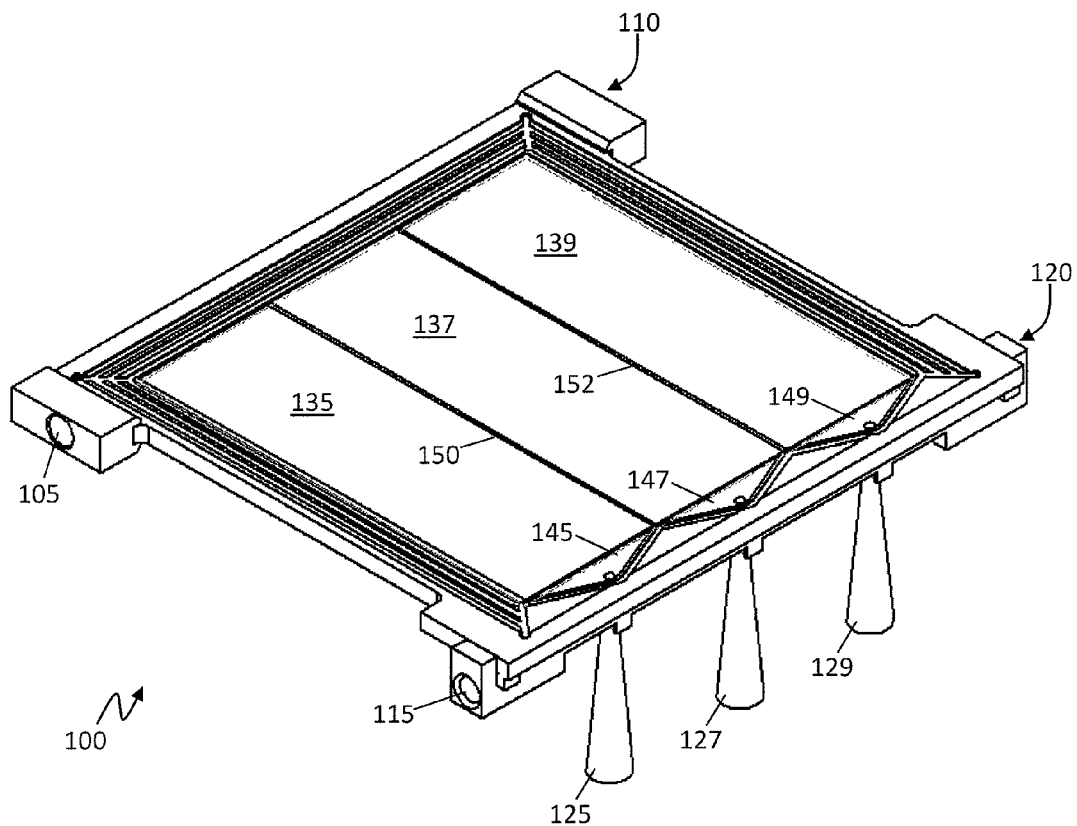
FIG. 1 illustrates an example embodiment of a flow cell having multiple separate flow regions.

In the present disclosure, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. The present disclosure describes embodiments of novel flow cells that may be used to conduct a variety of biochemical experiments and other biochemical operations.

Overview

As used herein, the term "flow cell" refers to a fluidic device that encloses a substrate (e.g., such as an array chip) under a coverslip. Preferably, the reaction chamber formed between the surface of the substrate and the coverslip is quite small (e.g., tens to several hundreds of microns) so that the pressure required to push a fluid through the reaction chamber gap may be high. Preferably, a pressure-driven system (e.g., comprising various types of pumps, valves, lines, and other fluid connections) is used to move fluids in and out of a flow cell; thus, a flow cell may also be referred to as a "closed" or "pressure-driven" fluidic device.

The flow cells described herein reduce consumption of expensive reagents and improve the yield of biochemical experiments that are conducted on the cell's substrate. Further, the flow cells described herein address the great commercial need that exists to increase the bio-reaction area of flow cells. For example, the described flow cells do not use artificial restrictors to dispense fluids onto their respective array chips. This provides for larger bio-reaction area that allows more experiments to be scanned by an imaging system with fewer flow cell changes, thus speeding up the overall data acquisition rate. In addition, the absence of artificial restrictors allows for substantially uniform dispensing of liquids across the flow cell chips, thereby ensuring substantially uniform conditions for the experiments that are conducted on the chip surfaces.

In some embodiments, the flow cells described herein are designed to use "make-and-break" seals during operation and thus do not need to be permanently attached to fluid connections such as tubing, lines, pumps, valves, etc. This allows the flow cells to be moved (e.g., by one or more robotic carriers or devices) from one station to another for performing various operations such as loading of different fluids, and also allows high-accuracy motion for image scanning. The temporary, when-needed fluidic connections facilitated by the use of the make-and-break seals allow for reducing the amount of fluids that are used, and can also reduce (or even eliminate) the need for cycles of washing the connections (for example, in configurations where each station is designated for dispensing only a single type of fluid).

Flow Cell with Inlet and/or Outlet Slit(s)

In one embodiment, a flow cell comprises a coverslip, a substrate disposed below the coverslip to form a reaction chamber, and an inlet manifold. The coverslip is made of transparent material that allows for optical detection of light or other radiation reflected or produced by biochemical experiments conducted in the reaction chamber. The substrate is disposed to partially cover the inlet manifold such that an inlet slit is formed along substantially the entire (inlet) edge of the substrate, where fluids can flow from the inlet manifold through the inlet slit, around the edge of the substrate, and into the reaction chamber. In this embodiment, the coverslip and the substrate may be disposed in a plastic housing, and the inlet manifold may be defined within the plastic housing such that the inlet slit is formed between the edge of the substrate and a side of a channel in the housing that defines the inlet manifold. In some implementations the housing may be a frame (e.g., without a bottom surface to support the substrate), while in other implementations the housing may provide a bottom surface or other structure(s) to support the substrate.

In some embodiments, the flow cell may comprise an outlet manifold that is defined on the outlet side of the substrate. The outlet edge of the substrate is disposed to partially cover the outlet manifold, thereby defining an outlet slit. The outlet slit is formed along substantially the entire (outlet) edge of the substrate such that fluids can flow from the reaction chamber around the outlet edge of the substrate, through the outlet slit, and into the outlet manifold.

Figure 5A:
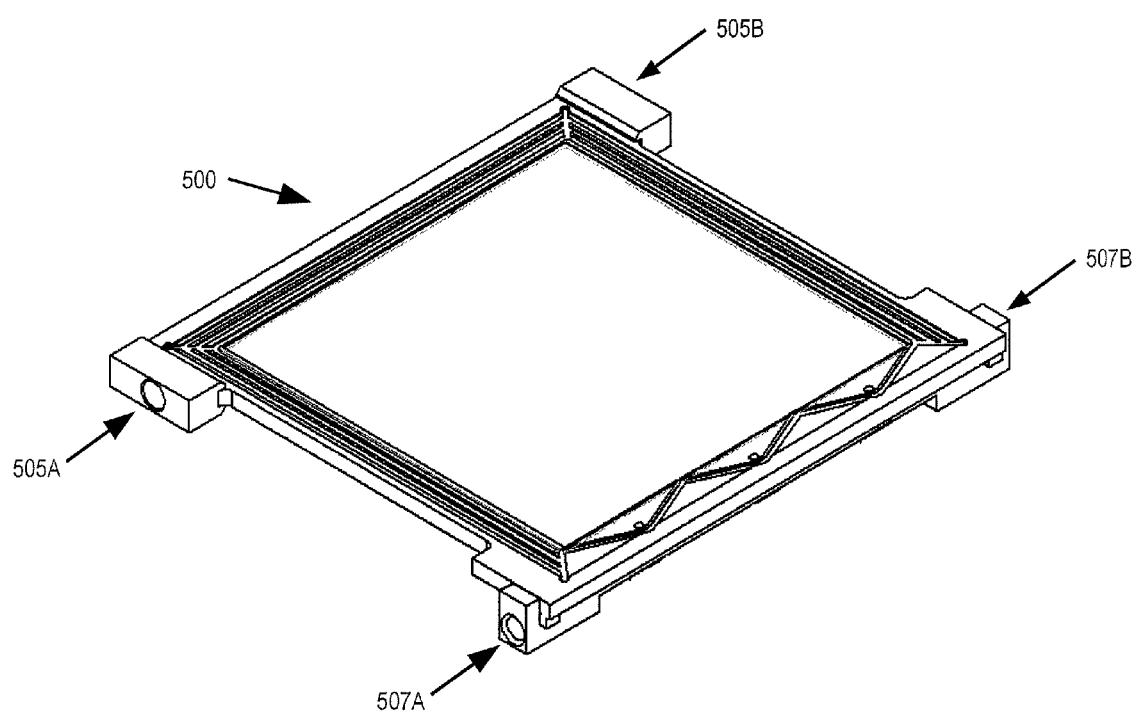
FIGS. 5A, 5B, 5C, 5D, and 5E illustrate details of an example embodiment of a flow cell having slit-like inlet and outlet channels.
Figure 5B:
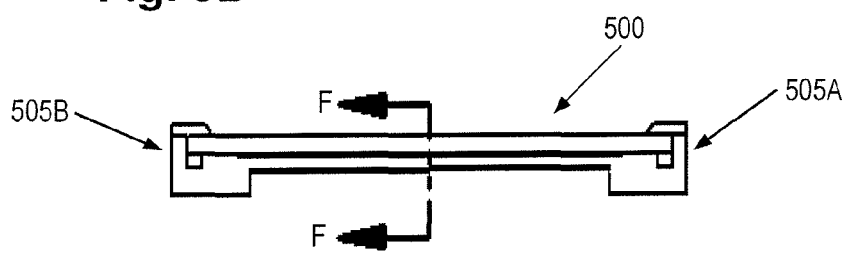
Figure 5C:
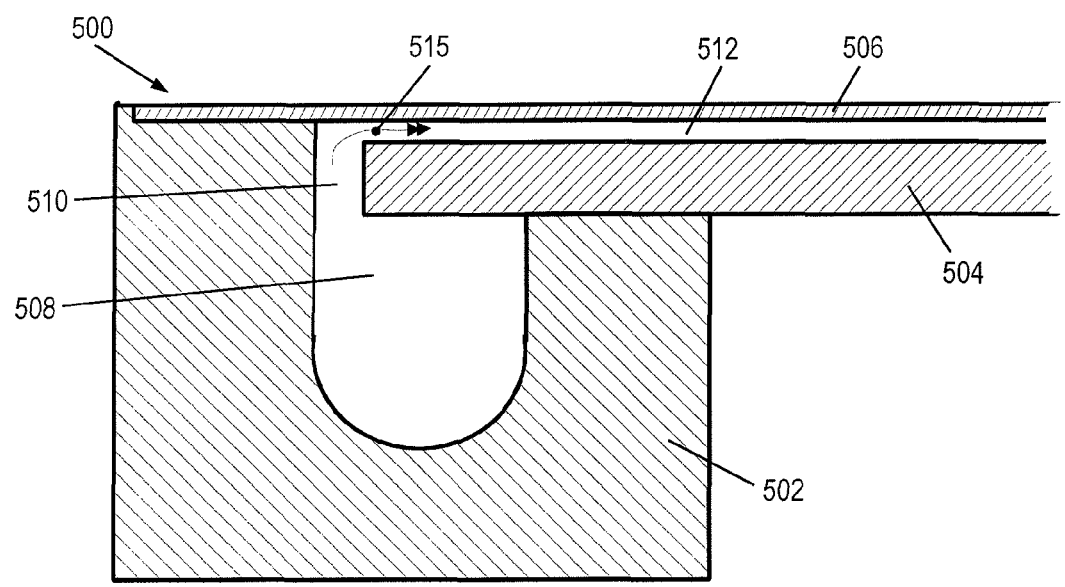
Figure 5D:
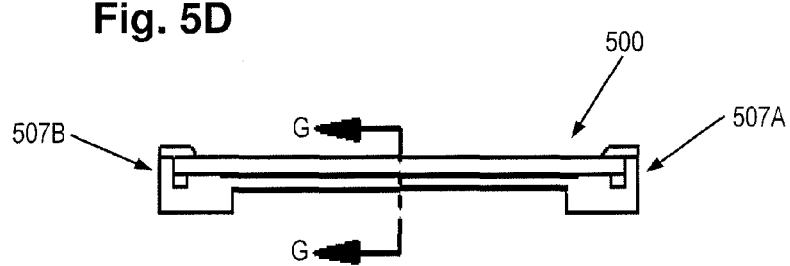
Figure 5E:
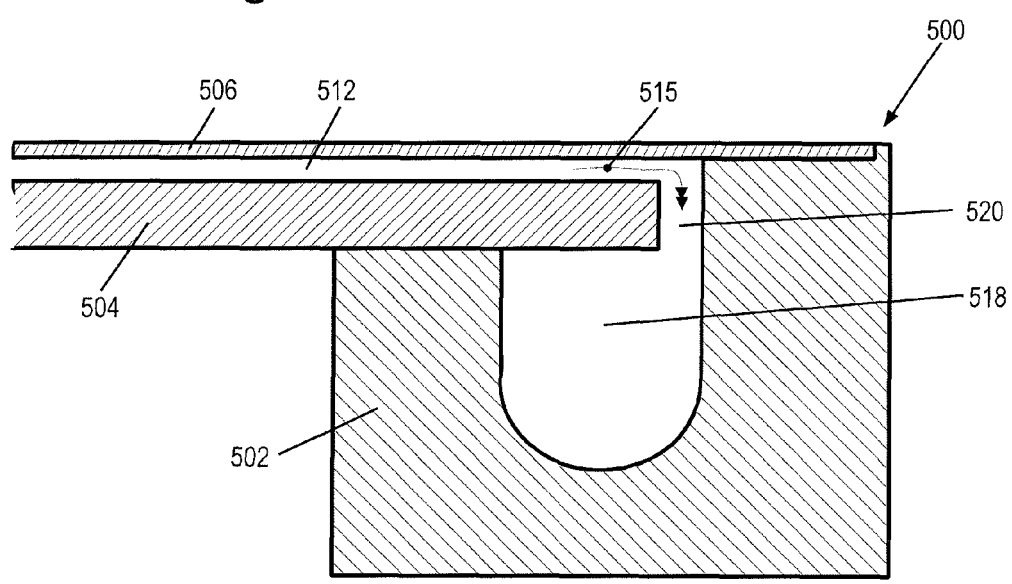

FIGS. 5A, 5B, 5C, 5D, and 5E illustrate details of an example embodiment of a flow cell having slit-like inlet and outlet channels. As illustrated in FIG. 5A, flow cell 500 comprises two inlet ports 505A and 505B that supply (and possibly drain) an inlet manifold, and two outlet ports 507A and 507B that drain (and possibly supply) an outlet manifold. FIG. 5B indicates a cross section of flow cell 500 that is perpendicular to and across the axis of inlet ports 505A and 505B, and FIG. 5C is a magnified view of part of the cross section indicated in FIG. 5B. FIG. 5D indicates a cross section of flow cell 500 that is perpendicular to and across the axis of outlet ports 507A and 507B, and FIG. 5E is a magnified view of part of the cross section indicated in FIG. 5D.

Referring to FIG. 5C, flow cell 500 includes substrate 504, coverslip 506, inlet manifold 508, and reaction chamber 512 that is formed between the coverslip and the substrate. In the embodiment illustrated in FIG. 5C, inlet manifold 508 is a channel that is machined, molded, or otherwise fabricated into housing 502; however, in different embodiments the inlet manifold may be disposed in a substrate or base that is separate from the flow cell housing. In the embodiment of FIG. 5C, coverslip 506 is permanently attached to the non-manifold sides or portions of housing 502 as part of assembling flow cell 500 (and therefore before any reagents or other fluids are disposed into the cell). For example, the coverslip may be attached to the non-manifold sides of the housing by glue lines and to the substrate by using glue dots and/or glue lines, where such glue dots and/or lines may include microspheres and/or other types of beads that are suitable to set the height of the reaction chamber to an appropriate size. In some embodiments, the housing of a flow cell may be made of a plastic that has chemical resistance to the various fluids that are used in biochemical reactions conducted in the flow cell; for example, the housing may be molded, machined, or otherwise made from a PEEK polymer.

Inlet slit 510 is formed between the edge of substrate 504 and the inner side of housing 502 that forms inlet manifold 508. Substrate 504 is disposed partially on top of inlet manifold 508, such that slit 510 is formed substantially along the entire length of the edge of substrate 504 along an axis that is parallel to the axis on which the two inlet ports 505A and 505B lie. In operation, a flow of fluids 515 enters reaction chamber 512 by flowing from inlet manifold 508, around the edge of substrate 504, and into reaction chamber 512. In other words, the fluids injected through the inlet port(s) 505A (and/or 505B) flow into reaction chamber 512 around the end of substrate 504.

Disposing substrate 504 partially on top of inlet manifold 508 (e.g., by leaving only inlet slit 510 open) allows the space in the manifold below the substrate to act as a bubble trap that traps bubbles in the fluid and as a conduit through which any bubbles can flow from one inlet port (e.g., 505A) to another port (e.g., 505B) without entering reaction chamber 512 through the slit. The bubble trap effect is caused because the fluid resistance of inlet slit 510 is higher than the fluid resistance in the conduit formed in inlet manifold 508. In some embodiments, the dimensions and the cross-section of the slit may be designed to be smaller than any expected bubbles, thereby presenting a further obstacle to any bubbles penetrating the reaction chamber.

The configuration of flow cell 500, as illustrated in FIG. 5C, allows for span-wise homogeneity and uniformity of the pressure of the fluid that flows into reaction chamber 512. For example, as compared to flow cells that use artificial restrictors, flow cell 500 achieves a much improved span-wise homogeneity and uniformity by having inlet slit 510 being disposed across the entire length of substrate 504 that is substantially parallel to the axis of inlet ports 505A-505B and substantially perpendicular to direction of the fluid flow into reaction chamber 512. In other words, the inlet slit creates a manifolding effect such that the fluid pressure is substantially equal along the entire length of the slit. This substantial pressure equalization is maintained by the reaction chamber itself, which acts as a manifold for the fluid that enters it through the slit. This configuration of flow cell 500 is different from other flow cell configurations that use holes or other artificial restrictors, in and/or onto the chip substrate, to create a manifolding effect in the reaction chamber.

In one embodiment, the configuration of the flow cell illustrated in FIG. 5C greatly reduces the chances of bubbles entering the reaction chamber, which allows the flow cell to use less reagent than other flow cells of comparable size. In this embodiment, bubbles may come from the fluid itself or may be intentionally placed into the fluid. For example, in this embodiment reagents may be fed into the flow cell through a tube, and a bubble may be placed between two reagents to separate them when the two reagents need to enter the reaction chamber in sequence. Since the manifold channel is placed (partially) under the backside (bottom side) of the substrate, any bubbles that may be present in the manifold would be prevented from entering the reaction chamber.

In some flow cell embodiments, the inlet manifold may be placed in a position relative to the substrate and the housing that is different than the position illustrated in FIG. 5C, but the inlet slit formed between them may still have a similar effect as described above. For example, the inlet manifold may be placed on the backside or above the substrate, and a slit of similar configuration as described above may be used as a conduit to load the reaction chamber of the flow cell in a similar manner.

FIG. 5E illustrates a cross-section of the outlet manifold side of flow cell 500. Flow cell 500 includes reaction chamber 512 that is formed between coverslip 506 and substrate 504, outlet manifold 518, and outlet slit 520. In the embodiment illustrated in FIG. 5E, outlet manifold 518 is a channel that is machined or molded into housing 502; however, in different embodiments the outlet manifold may be disposed in a substrate or base that is separate from the flow cell housing.

Outlet slit 520 is formed between the edge of substrate 504 and the inner side of housing 502 that forms outlet manifold 518. Similarly to the inlet manifold side of flow cell 500, substrate 504 is disposed partially on top of outlet manifold 518, such that slit 520 is formed substantially along the entire length of the edge of substrate 504 along an axis that is parallel to the axis on which the two outlet ports 507A and 507B lie. In operation, fluids 515 (which have entered reaction chamber 512 from the inlet manifold) flow around the edge of substrate 504, through outlet slit 520, and into outlet manifold 518. In other words, the fluids flow out of reaction chamber 512 around the edge, and then under the backside (bottom side), of substrate 504.

In some flow cell embodiments, the outlet manifold may be placed in a position relative to the substrate and the housing that is different than the position illustrated in FIG. 5E, but the outlet slit formed between them may still have a similar effect as described above. For example, the outlet manifold may be placed on the backside or above the substrate, and an outlet slit of similar configuration as described above may be used as a conduit to drain fluids from the reaction chamber in a similar manner.

In the embodiment illustrated in FIGS. 5A-5E, substrate 504 is preferably made of silicon and coverslip 506 is preferably made of glass; in other embodiments the substrate of a flow cell can be made of a reflective metal such as aluminum or titanium, and the coverslip may be made of other transparent materials with optical qualities that are suitable for the desired use (e.g., for optical observation and signal detection). Preferably, the length and width of housing 502 is between 1 inches and 4 inches, the thickness of substrate 504 is between 600 µm and 800 µm, the thickness of coverslip 506 is between 150 µm and 200 µm, and the height of reaction chamber 512 is between 20 µm and 60 µm. The dimensions of inlet slit 510 are preferably between 100 µm and 1.5 mm and its cross-sectional ratio of length to width is preferably about 1:5. Outlet slit 520 has similar dimensions and cross-sectional ratio of length to width. It is noted that other flow cell embodiments may use housings, substrates, coverslips, reaction chambers, inlet slits, and outlet slits that have different and varying dimensions, and for this reasons the dimensions described herein are to be regarded in an illustrative rather than a restrictive sense.

For example, in various embodiments the length and width of a flow cell substrate may be in a range from 100 µm to 12 cm or in any sub-range in-between (e.g., for silicon-based substrates), and in ranges from 10 mm up to even 50 cm (e.g., for coated-glass substrates); in these embodiments, the lengths and widths of the corresponding coverslip and housing may be within corresponding ranges that are suitable for providing the flow cell with mechanical/structural support and the functionalities described herein.

In various embodiments, the height of the reaction chamber in a flow cell may be defined by one or more spacers that connect the reaction surface of the substrate to the bottom surface of the coverslip, such that the warping of the coverslip over any given portion of the substrate is within the range from 0% to 25% of the height of the reaction chamber. For example, in a flow cell embodiment that uses a substrate that is about 3" (inch) by 3" (e.g., about 66.2 mm by 77.2 mm) and a coverslip with a thickness of 120 µm, 58 glue dots may be used as spacers that are positioned in a regular pattern on the substrate at about 1 cm apart. In other embodiments, various numbers of spacers may be positioned on the substrate at distances that range from 2 mm to several centimeters apart.

In various embodiments, a flow cell may be designed such that its reaction chamber can substantially support internal pressure in a range from 0 kPa to 200 kPa. For example, the over-pressure (e.g., pressure above standard atmospheric pressure, or 101.325 kPa) that a flow cell can withstand may be defined by the strength with which spacers (or other connectors) couple the coverslip and the substrate to form the reaction chamber; the under-pressure (e.g., pressure less than 20 kPa) that a flow cell can withstand may be defined by the thickness of the coverslip and the height of the reaction chamber.

In various embodiments, a large number of attachment sites may be configured on the flow cell substrate in regular or random patterns, where the number of attachment sites may preferably be in a range from 5 billion to 50 billion, and more preferably in a range from 10 billion to 15 billion, and more generally in any sub-ranges in-between; in embodiments that use regular patterns, the pitch between the centers of any two adjacent attachment sites may be in a range from 250 nm to 1.5 µm. (For example, a flow cell embodiment with about 3" by 3" substrate may have 13.8 billion attachment sites configured thereon as an array with a pitch of 620 nm.) In operation, when macromolecules or other target nucleic acids are disposed on the attachment sites, various flow cell embodiments preferably provide single-molecule occupancy at 60% to 95% of the attachment sites; further, the yield (e.g., the average number of macromolecules or target nucleic acids that emit a signal at any given imagining run) in various flow cell embodiments may preferably be in a range from 35% to 65% of all attachment sites that hold macromolecules or target nucleic acids.

In various embodiments, the size of the inlet and/or outlet manifold(s) of a flow cell may range from 20 µm to 2 mm, where the size may be expressed as a diameter (e.g., for manifolds with circular/semicircular cross section) or as depth/width (e.g., for manifolds with channels having other types of cross-section). In some embodiments, the inlet and/or outlet manifold(s) may have at least partially a semi-circular cross-section with a diameter value that is a function of the height of the reaction chamber. For example, the diameter of the manifold cross-section may range anywhere from 2 times the reaction chamber height to 10 times the reaction chamber height.

In various embodiments, the width of the inlet and/or outlet slit(s) of a flow cell may preferably be in a range from 10 µm to 1 mm, and more preferably in a range from 50 µm to 500 µm. In some embodiments, the width of the inlet and/or outlet slit(s) may be defined as a function of the height of the reaction chamber and the diameter (or size) of the corresponding inlet/outlet manifold in order to take into account the types of fluids (and therefore the types of bubbles that can form therein) which the flow cell is designed to process. For example, the width of the slit may be defined to range from a value representing the height of the reaction chamber to a value that is one half of the width of the corresponding manifold channel; that is, the slit width may be a value between the reaction chamber height and ½ of the manifold channel width.

Flow Cell with Multiple Flow Regions

In one embodiment, a flow cell for multi-sample sequencing includes multiple injection ports and flow region dividers so that DNA fragments from different samples are kept separate during loading while allowing parallel biochemical processing across genomes during subsequent processing.

FIG. 1 illustrates a flow cell having multiple, separate flow regions. In FIG. 1, flow cell 100 uses a four-port design to create a fluid line source and line sink that are connected to respective manifolds. An inlet manifold is supplied and drained by inlet ports 105 and 110 (partially hidden in perspective view) while an outlet manifold is supplied and drained by outlet ports 115 and 120 (partially hidden in perspective view). The flow cell of FIG. 1 is an example having three separate flow regions formed between a substrate and a coverslip; however, a similar cell may be designed with as few as two, or as many as dozens, of flow regions. Loading tips 125, 127 and 129 are used to load macromolecules or other target nucleic acids into flow regions 135, 137, and 139, respectively. Flow distribution funnels 145, 147, and 149 spread liquid flow from the loading tips to the flow regions. Dividers 150 and 152 separate flow regions 135, 137, and 139 from one another. In one implementation, dividers 150 and 152 are made of glue that contains microspheres to set the appropriate height of the reaction chambers that are formed in the flow regions between the substrate and the coverslip.

Flow cell 100 allows solutions of macromolecules or other target nucleic acids to be loaded into specific flow regions using loading tips. In an initial loading step, the solutions flow from the loading tips into the flow regions and drain out in the inlet manifold. In later processing steps the loading tips are replaced by plugs. Reagents, buffers, and other reaction fluids are then introduced into the inlet manifold through inlet ports 105 and/or 110, flow through all of the multiple regions, and drain into the common outlet manifold 210. Thus, the flow direction of the solution in the loading step is opposite from the flow direction of reagents, buffers, and other reaction fluids in later processing steps.

FIGS. 2A, 2B, and 2C show details of the outlet manifold of the flow cell of FIG. 1 during loading. FIG. 2A is a side view of flow cell 100; FIG. 2B is a cross section of FIG. 2A as indicated in the drawings; FIG. 2C is a magnified view of part of FIG. 2B as indicated in the drawings. In FIG. 2C, loading tip 127 is shown inserted through common outlet manifold 210 into loading port 205. Loading port 205 is connected to flow distribution funnel 147 (see FIG. 1) which feeds flow region 137. Loading port 205 is sealed by loading tip 127 such that fluid in the tip does not leak into common outlet manifold 210 during loading. Small arrows in FIG. 2C represent fluid flow during loading. Fluid flows in the reaction chambers formed in the flow regions between coverslip 220 and substrate 230.

Fluid supplied to flow region 137 via distribution funnel 147 and loading tip 127 does not mix with fluid from other loading tips. Once flow region 137 is filled by fluid supplied by loading tip 127, excess fluid drains out through the inlet manifold and inlet ports 105 and 110. Similarly, flow regions 135 and 139 also drain into the inlet manifold. The inlet manifold serves as a line sink, or drain, during flow cell loading from the loading tips.

After loading is complete, the loading tips are removed and replaced by plugs. The plugs seal off holes in the common outlet manifold through which the loading tips were inserted, but leave the outlet manifold open to the various loading ports.

FIGS. 3A, 3B, and 3C show details of the outlet manifold of the flow cell of FIG. 1 when it is plugged. FIG. 3A is a side view of flow cell 100 similar to FIG. 2A but with loading tips removed; FIG. 3B is a cross section of FIG. 3A as indicated in the drawings; FIG. 3C is a magnified view of part of FIG. 3B as indicated in the drawings. Small arrows in FIG. 3C indicate fluid flow during fluid processing. Fluid flows in the reaction chamber between coverslip 220 and substrate 230 in flow region 137 into loading port 205 and outlet manifold 210. Plug 305 prevents fluid from leaking out. Outlet manifold 210 connects all of the loading ports in the flow cell and is supplied and drained by outlet ports 115 and 120.

No solid structure prevents fluid from flowing out of flow region 137, into outlet manifold 210 and then into another flow region. However, such flow from one region back into another via the outlet manifold is extremely unlikely because the fluid resistance in the outlet manifold is significantly lower than in any flow region. The flow regions are supplied with reagents, buffers, and other reaction fluids from the common inlet manifold that is supplied and drained by inlet ports 105 and 110.

Figure 4A:
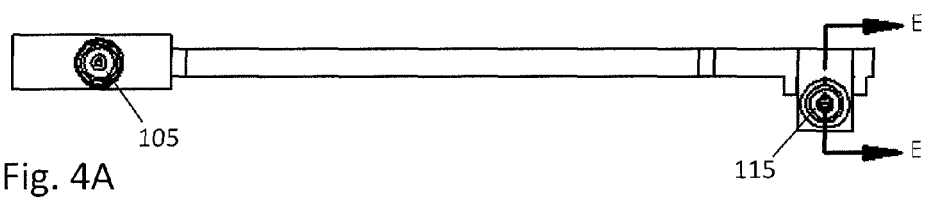
FIGS. 4A and 4B illustrate another view of the flow cell of FIG. 1 and its outlet manifold.
Figure 4B:
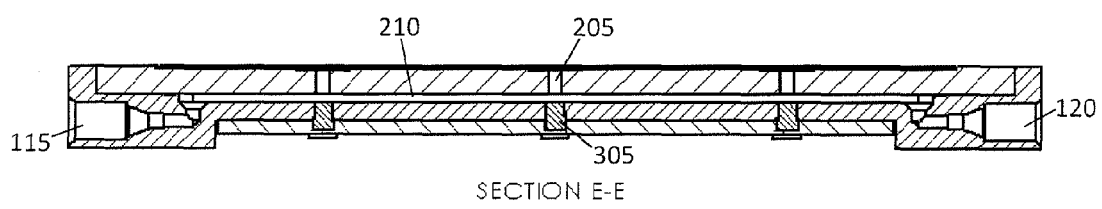

FIGS. 4A and 4B show another view of the flow cell of FIG. 1 and its outlet manifold. FIG. 4A is a side view of flow cell 100; FIG. 4B is a cross section of FIG. 4A as indicated in the drawings. FIG. 4B shows how common outlet manifold 210 is connected to loading ports such as loading port 205. The outlet manifold is also plugged by plugs such as plug 305. Finally, the outlet manifold is supplied and drained by outlet ports 115 and 120.

Although the flow cell of FIG. 1 has been described in terms of loading and processing multiple samples, clearly it may be used in any situation where separation between flow regions is desired for some steps in a microfluidic process but not for others. For example, loading tips may be inserted for any steps in a process for which separation between flow regions is desired.

In the embodiments illustrated in FIGS. 1-4, substrate 230 is preferably made of silicon and coverslip 220 is preferably made of glass; in other embodiments the substrate of a flow cell can be made of a reflective metal such as aluminum or titanium, and the coverslip may be made of other transparent materials with optical qualities that are suitable for the desired use (e.g., for optical observation and signal detection).

Various flow cell embodiments may use housings, substrates, coverslips, and reaction chambers that have different and varying dimensions, and for this reasons the dimensions provided hereinafter are to be regarded in an illustrative rather than a restrictive sense.

For example, in various embodiments the length and width of a flow cell substrate may be in a range from 100 µm to 12 cm or in any sub-range in-between (e.g., such silicon-based substrates), and in ranges from 10 mm up to even 1 meter (e.g., for coated-glass substrates); in these embodiments, the lengths and widths of the corresponding coverslip and housing may be within corresponding ranges that are suitable for providing the flow cell with mechanical/structural support and the functionalities described herein.

In various embodiments, the height of the reaction chamber in a flow cell may be defined by one or more spacers that connect the reaction surface of the substrate to the bottom surface of the coverslip, such that the warping of the coverslip over any given portion of the substrate is within the range from 0% to 25% of the height of the reaction chamber. For example, glue dots may be used as spacers that are positioned in a regular pattern on the substrate at about 1 cm apart. In other embodiments, various numbers of spacers may be positioned on the substrate at distances that range from 2 mm to several centimeters apart.

In various embodiments, a flow cell may be designed such that its reaction chamber can substantially support internal pressure in a range from 0 kPa to 200 kPa. For example, the over-pressure (e.g., pressure above standard atmospheric pressure, or 101.325 kPa) that a flow cell can withstand may be defined by the strength with which spacers (or other connectors) couple the coverslip and the substrate to form the reaction chamber; the under-pressure (e.g., pressure less than 20 kPa) that a flow cell can withstand may be defined by the thickness of the coverslip and the height of the reaction chamber.

In various embodiments, a large number of attachment sites may be configured on the flow cell substrate in regular or random patterns, where the number of attachment sites may preferably be in a range from 5 billion to 50 billion, and more preferably in a range from 10 billion to 15 billion, and more generally in any sub-ranges in-between; in embodiments that use regular patterns, the pitch between the centers of any two adjacent attachment sites may be in a range from 250 nm to 1.5 µm. In operation, when macromolecules or other target nucleic acids are disposed on the attachment sites, various flow cell embodiments preferably provide single-molecule occupancy at 60% to 95% of the attachment sites; further, the yield (e.g., the average number of macromolecules or target nucleic acids that emit a signal at any given imaging run) in various flow cell embodiments may preferably be in a range from 35% to 65% of all attachment sites that hold macromolecules or target nucleic acids.

Make-and-Break Seals

In contrast to approaches that use permanent tubing to fluidicly connect to a stationary flow cell, the flow cells described herein are configured for use with make-and-break seals so that a flow cell does not need to be stationary throughout the cycle runs in which the flow cell is used in an apparatus.

According to one embodiment, a make-and-break seal is used to temporarily and reversibly couple a flow cell to an apparatus or a station thereof when the flow cell is loaded/unloaded with fluids. The inlet ports of the flow cell are adapted to receive injector component(s) that have make-and-break seals mounted thereon in order to receive reagents and/or other fluids from the injector component(s) and through respective openings in the seals that match corresponding channels through the inlet ports. After the flow cell is loaded with the desired fluid(s), the injector component(s) with the make-and-break seals are decoupled from the flow cell, and the flow cell can then be moved to a different station in the same or a different apparatus. The make-and-break seals can be made of rubber or other elastomer in a shape that fits into the sockets of the inlet and/or outlet flow cell ports.

For example, one or more source and drain components with make-and-break seals may be engaged to a flow cell, and the source component(s) may inject one or more fluids in the flow cell. After the flow cell is loaded with fluid(s) and the source and drain component(s) with the make-and-break seals are disengaged from the flow cell, the flow cell can be physically moved by a lab robot or another transport device from its current location to a physically separate and different station. This allows for decoupling the flow cell from the stations that process the flow cell. Such decoupling may be beneficial in DNA sequencing. For example, using make-and-break seals for loading/unloading a flow cell allows the station or portion of the sequencing apparatus (e.g., such as an imaging device) that takes snapshots of the biochemical experiments conducted in the flow cell to be insulated from vibrations and other side effects that may be caused by a component which prepares the flow cell for sequencing (e.g., such as a reaction sub-system). In another example, using make-and-break seals to load/unload a flow cell provides for better scaling since an arbitrary number of flow cells can be automatically mounted on different stations of the same sequencing apparatus, thereby allowing the apparatus to operate continuously without the need to stop for decoupling of the flow cells from persistent fluid connections.

In an example embodiment, a flow cell configured to use make-and-break seal(s) is injected with different types of reagent fluids at different stations of the same or a different apparatus. Since after being loaded with fluid the flow cell is effectively sealed by micro-capillary forces acting in and on the inlet and outlet ports, the flow cell can be moved to different stations, thereby allowing for each separate station to inject a separate reagent fluid or fluids. Thus, in contrast to conventional approaches (which use the same tubing to bring all necessary fluids to the flow cell), the approach described herein of using make-and-break seals to load/unload flow cells allows a flow cell to be physically moved to and from the different stations that dispense different types of fluids. This is beneficial in DNA sequencing because it avoids the need to flush clean the common tubing that conventional approaches use to connect to a stationary cell, thereby reducing the amount (and therefore the costs) of the used reagents.

Figure 6A:
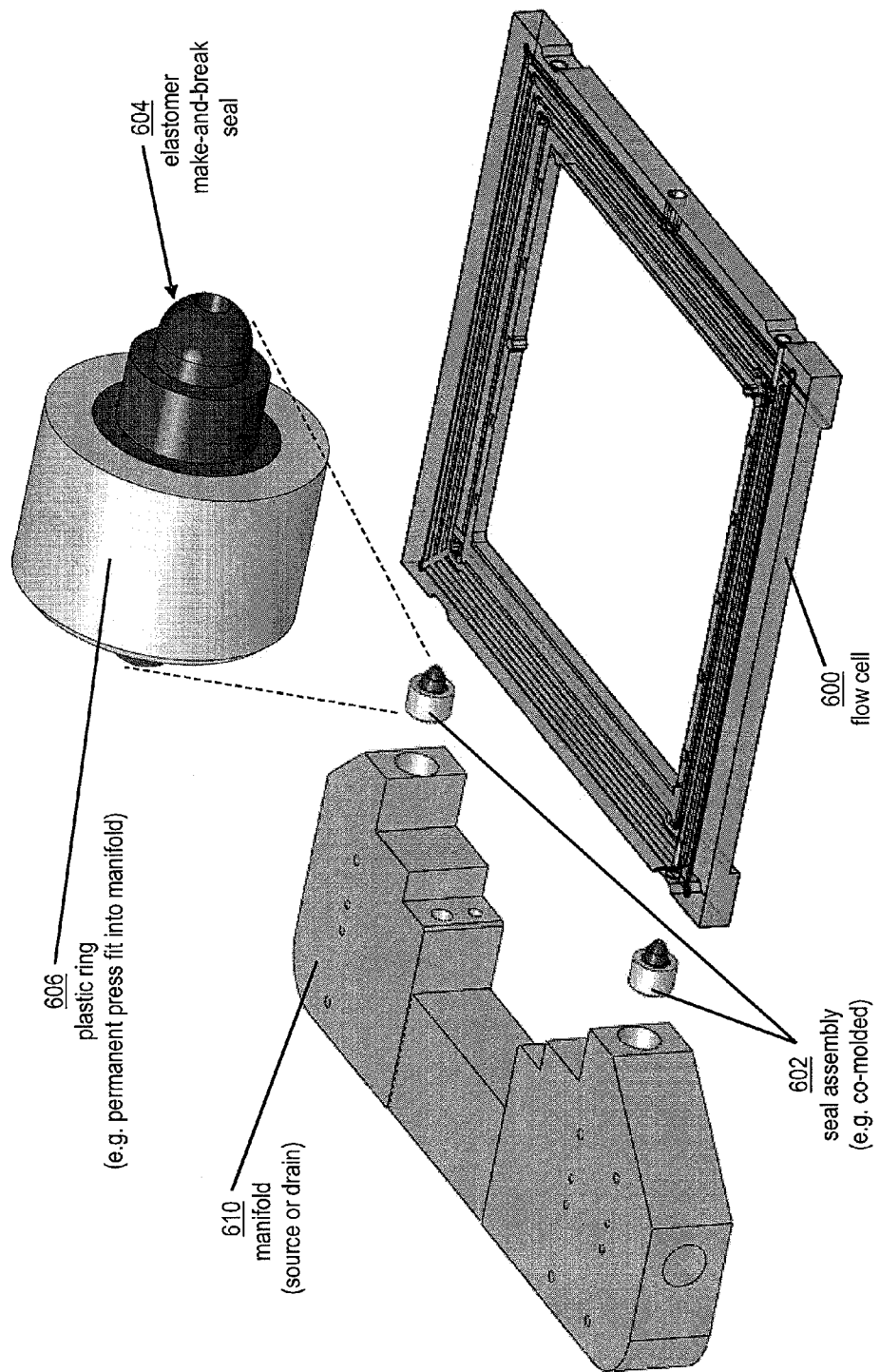
FIG. 6A is an isometric view of an example make-and-break seal that can be used in conjunction with a flow cell according to one embodiment.

FIG. 6A illustrates an isometric view of an example make-and-break seal that can be used in conjunction with a flow cell according to one embodiment.

Flow cell 600 is configured with inlet and outlet ports and manifolds as described in the previous sections. In operation, seal assemblies 602 are engaged with the corresponding sockets of the ports in flow cell 600 when the flow cell is being loaded with fluids through source manifold 610. (FIG. 6A illustrates manifold 610 as being a source manifold through which flow cell 600 is loaded with fluids. It is noted, however, that a drain manifold having similar structure and seal assemblies is coupled to the opposite end of the flow cell to capture any fluid that drains out of the flow cell. Thus, as used herein, "source" and "drain" are used with respect to the direction of the fluid flow and generally reflect the manifolds where the fluid starts and where it ends, respectively.)

A seal assembly 602 comprises a make-and-break seal 604 and a plastic ring 606. Seal assembly 602 is manufactured by co-molding seal 604 with ring 606, where the seal is made from a suitable elastomer and the ring is made from a suitable plastic material. For example, ring 606 can be made from PEEK or other plastic that has biocompatible and chemically inert properties.

Make-and-break seal 604 is annular in cross-section such that an opening extends within and across the entire length of the seal. Seal 604 has a hemispherical shape at one of its ends such the cross-section area of at least a portion of the seal decreases along the seal length in the direction of the seal tip. Thus, the sealing surface of seal 604 is hemispherical and is configured to fit into a similarly shaped socket in the corresponding inlet port of flow cell 600. In the embodiment illustrated in FIG. 6A, the manifold end of seal assembly 602 comprises a seal (the manifold seal) that is coupled to a corresponding opening in source manifold 610; the manifold seal has a shape that is similar to the seal that couples to the flow cell (the flow-cell seal).

Seal assembly 602 is manufactured by first co-molding seal 604 and the plastic ring 606. Ring 606 may then be machined (if necessary), and the resulting seal assembly is then permanently attached (e.g., by glue or a mechanical press fit) into a corresponding opening in manifold 610. The manifold end of seal assembly 602 (i.e., the end of the seal assembly that is fitted into the source or drain manifold) includes a manifold seal essentially having the same shape and form as the seal that couples to the flow cell (the flow-cell seal). It is noted that in a preferred embodiment the manifold seal is permanently fit into manifold 610 in order to simplify the manufacturing process. For example, since co-molding is a high-temperature process, co-molding the seal directly into the source (or drain) manifold may deform the manifold in an unpredictable manner. Thus, the co-molding approach described herein avoids this problem by first co-molding the seal with the plastic ring into a seal assembly, and then permanently pressing the plastic ring into a corresponding socket into the manifold. It is noted, however, that this co-molding approach is only one example of a technique that can be used to manufacture a make-and-break seal and should be regarded in an illustrative rather than a restrictive sense because one of skill in the art may design other approaches without undue effort or experimentation.

For example, in some embodiments a flow seal assembly (e.g., such as assembly 602 in FIG. 6A, or another type of assembly) may be permanently attached (e.g., by glue or a mechanical press fit) into a corresponding socket of a fluidic port in the flow cell, so that in operation the flow-cell seal of the assembly is permanently attached to the flow cell and the manifold seal of the assembly is engaged and subsequently disengaged from an opening in the source (or drain) manifold. In yet other embodiments, a flow seal assembly (e.g., such as assembly 602 in FIG. 6A, or another type of assembly) is not permanently attached to either the flow cell or the source/drain manifold. Rather, in these embodiments the flow seal assembly may be mounted on a mechanism (e.g., such as a motorized stage or other precision-controlled device) that can be aligned with high precision to the receptacle openings in the flow cell and in the source (or drain) manifold. During loading and unloading operations, in these embodiments the flow-cell seal of the assembly is engaged to the flow cell and the manifold seal of the assembly is engaged to the source (or drain manifold), and subsequently both the flow-cell seal and the manifold seal are disengaged from the flow cell and the source (or drain) manifold, respectively.

Figure 6B:
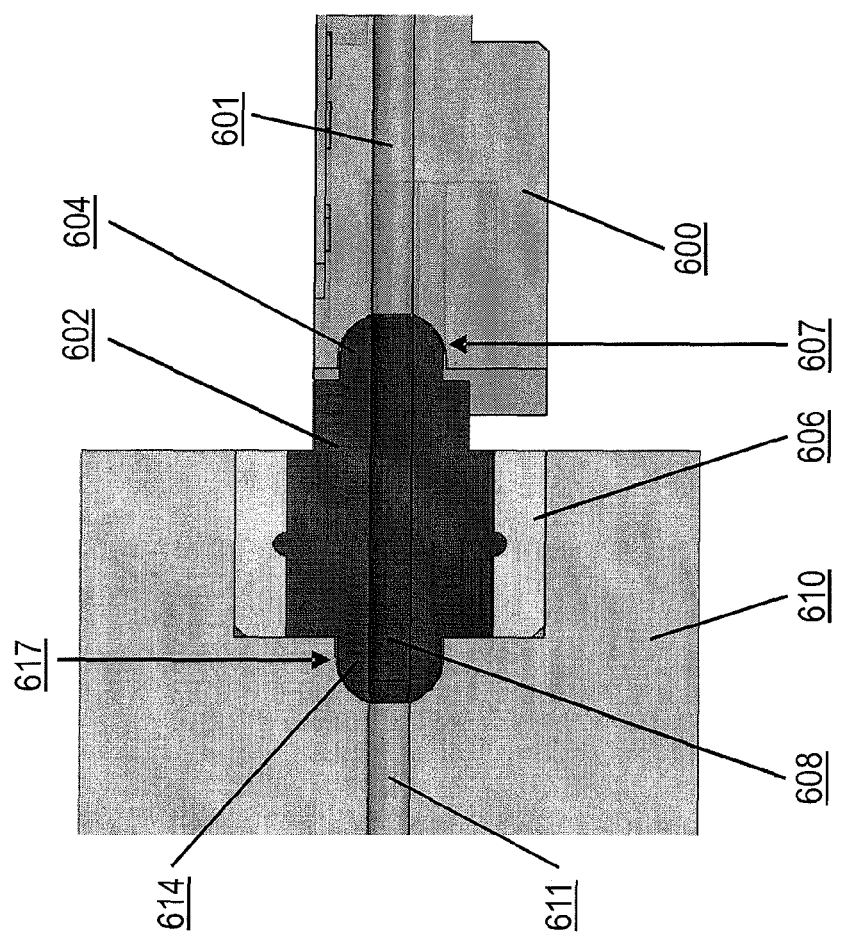
FIG. 6B is a cross-sectional view of an example make-and-break seal as pressed into a source manifold and seated against a flow cell according to the embodiment of FIG. 6A.

FIG. 6B illustrates a cross-sectional view of an example seal assembly 602 according to the embodiment of FIG. 6A as the seal 604 is engaged against flow cell 600. In the embodiment illustrated in FIGS. 6A and 6B, seal 604 has a diameter of 2 mm at its widest cross-section with an acceptable tolerance range of ±0.050 mm. Channel 608, which extends through the length of seal assembly 602 (and through flow-sell seal 604 and manifold seal 614), has a diameter of 0.8 mm with an acceptable tolerance range of ±0.025 mm. Channel 601 (in the flow port of flow cell 600) and channel 611 (in manifold 610) have the same diameter as channel 608—that is, a diameter of 0.8 mm with an acceptable tolerance range of ±0.025 mm. The length of the hemispherical portion flow-sell seal 604 and manifold seal 614 is about 1.92 mm with an acceptable tolerance range of ±0.050 mm. The radius of the hemispherical portions of flow-cell seal 604 and manifold seal 614 is about 1 mm with an acceptable tolerance range of ±0.025 mm.

Manifold 610 comprises socket 617, into which the manifold seal 614 is permanently pressed. Socket 617 includes a hemispherical section having a diameter that is slightly bigger than the diameter of the hemispherical portion of the manifold seal 614. For example, at its widest cross-section, the diameter of the hemispherical section of socket 617 is about 2.1 mm and is thus 100 μm bigger than the diameter of the corresponding hemispherical section of manifold seal 614; this allows for an acceptable ±50 μm radial misalignment between the manifold seal 614 and socket 617. Similarly, at its widest cross-section, the diameter of the hemispherical section of socket 607 (in flow cell 600) is about 2.1 mm and is thus 100 μm bigger than the diameter of the corresponding hemispherical section of seal 604; this allows for an acceptable ±50 μm radial misalignment between seal 604 and socket 607 when the seal is engaged with flow cell 600 during loading/unloading operations. Further, when engaged with flow cell 600 during loading/unloading operations, the angular misalignment between seal 604 and socket 607 may be in the range of ±1° (i.e., plus or minus one degree).

More generally, in various embodiments the dimensions of make-and-break seals (and of the corresponding sockets and channels) depend on the dimensions of the flow cells (and of the manifolds thereof) with which the seals are intended to be used. For example, the size of manifold channels in a flow cell may range from 20 μm to 2 mm, and therefore the make-and-break seals (and the corresponding sockets and channels) should have dimensions that are suitable for proper sealing during loading/unloading operations. Further, in various embodiments the shapes of make-and-break seals (and of the corresponding sockets and channels) may depend on the particular fluids with which the seals are intended to be used. For example, in some embodiments the make-and-break seals may have a flat shape, while in other embodiments the make-and-break seals may be conical in shape. Thus, the examples of dimensions and shapes of make-and-break seals described herein are to be regarded in an illustrative rather than a restrictive sense.

In various embodiments, an example parameter that governs the proper operation of a make-and-break seal is the hardness of the material from which the seal is made. An example of a hardness measure is the "Shore" measure according to ISO 868. In general, Shore hardness is a measure of the resistance of a material to a given force. Shore hardness is determined as a number from 0 to 100 on the scales A or D, where a higher number indicates higher hardness and the letter A is used for flexible plastic materials while the letter D is used for more rigid plastic materials. In an example embodiment, a make-and-break seal may be manufactured from an elastomer having a Shore A value of 63. Other suitable compounds for manufacturing the seal include elastomers with Shore A values in the range from 55 to 75.

In various embodiments, one parameter that governs proper sealing is referred to as "percentage compression". Percentage compression is expressed as $$P = \left(1 - \frac{L_{engaged}}{L}\right) * 100$$

where P is the percentage compression value, L is the original length of the seal, and $L_{engaged}$ is the length of the seal when the seal is engaged during loading/unloading operations. In order to achieve a proper sealing function, the preferable (but not exclusive) percentage compression should be in the range from 10% to 20% (e.g., for a seal made from material with hardness in the range between 55-75 Shore A), which means that during operation the seal is compressed from its original length to a length in the range of 90% to 80% of its original length. While percentage compression outside the 10-20% range may work in some embodiments, generally a coupling pressure on the seal (e.g. against the flow cell port) that causes a percentage compression less than 10% may result in leakage due to insufficient sealing. Similarly, a coupling pressure on the seal that causes a percentage compression higher than 20% may cause the seal to distort, which in turn can lead to leaking or to partially or fully closing the flow cell port (because the tip of the seal would get pressed into the port opening); in addition, such misalignment of the port opening and the seal channel may cause an edge of the seal to get in the way of the fluid flow and/or to catch a bubble. It is noted that in various embodiments the optimal range for percentage compression may depend on the hardness of the material from which a seal is made—for example, percentage compression may be higher than 20% for softer materials and lower than 10% for harder materials.

An example of a seal design that takes into account percentage compression is illustrated in the embodiment of FIG. 6B. In this embodiment, the length of flow-cell seal 604 is about 1.92 mm and the length of socket 607 (in the port of flow cell 600) is about 1.63 mm (with an acceptable tolerance range of range of ±0.025 mm). In operation, seal 604 is pressed into socket 607 all the way to the seal shoulder, which results in percentage compression value of $$P = \left(1 - \frac{1.63}{1.92}\right) * 100 \approx 15.1\%$$

Further, the manifold seal 614 has substantially the same length as seal 604, and the length of socket 617 (in manifold 610) is substantially the same as the length of socket 607; thus, the permanent press fitting of assembly 602 into manifold 610 also results in seal 614 having a percentage compression of approximately 15%. More generally, in various embodiments that make use of manifold seals, it is preferable for such seals to have a percentage compression in the range from 10% to 20%, which is likely to ensure sufficient sealing function.

In some embodiments, an example parameter that may govern proper sealing is the area (and/or volume) ratio between the surface (and/or volume) of the seal and the surface (or volume) of the corresponding socket that is configured to receive the seal. For example, in some embodiments this area (and/or volume) ratio should be such that as the distance between the shoulder of the seal and the shoulder of the corresponding socket goes down to 0 when the seal is being engaged, the seal achieves a 10% to 20% percentage compression. Configuring this ratio parameter based on the area (and/or volume) ratio may be used, for example, in embodiments in which the coupling of the seal to the flow cell port is controlled by components that provide a kinematic interface. For example, such embodiments may use interface components to engage the make-and-break seal with a flow cell based on kinematic controls. Rather than measuring and controlling the right amount of force with which to push the seal into the corresponding socket, these embodiments use one or more system components (actuators, pistons, etc.) that are configured to push the seal until the shoulder of the seal touches the shoulder of the flow cell so that any further application of force would not cause any further compression of the seal.

In some embodiments, the coupling of the make-and-break seal to the flow cell port may be controlled by a precise-force interface. In these embodiments, the coupling (or engagement) of the seal to the flow cell port may be controlled by components that directly measure the force applied to the seal as the seal is engaged with the flow cell. For example, such force, when applied to engage the seal to the flow cell, may be in the range from 0.25N (Newtons) to 0.55N in order to achieve proper sealing function.

Other examples of parameters that may govern the proper operation of a make-and-break seal may include various properties of the material from which a make-and-break seal is manufactured. For example, for any particular implementation, a suitable material for a make-and-break seal may be any elastomer that is bio-compatible with the reagents and other fluids used in such implementation and/or that is inert with respect to the chemical properties of such reagents and fluids.

Figure 7A:
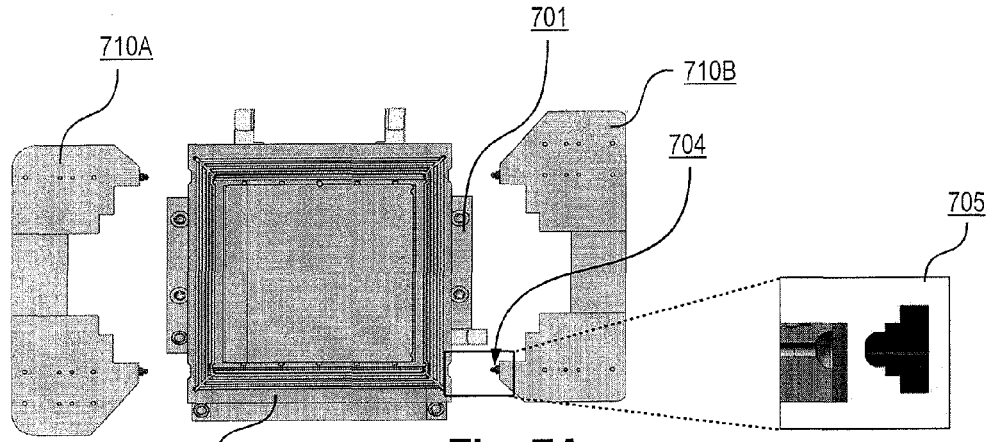
FIGS. 7A, 7B, and 7C show details of using make-and-break seals to load a flow cell in accordance with an example embodiment.
Figure 7B:
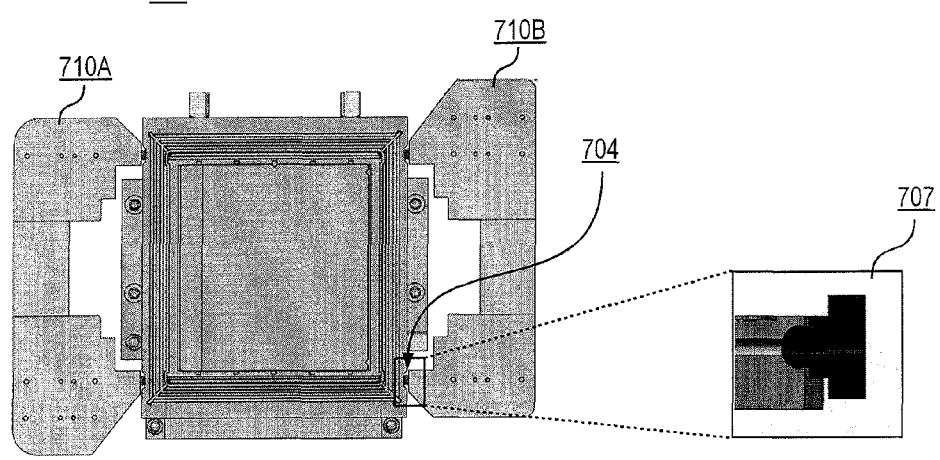
Figure 7C:
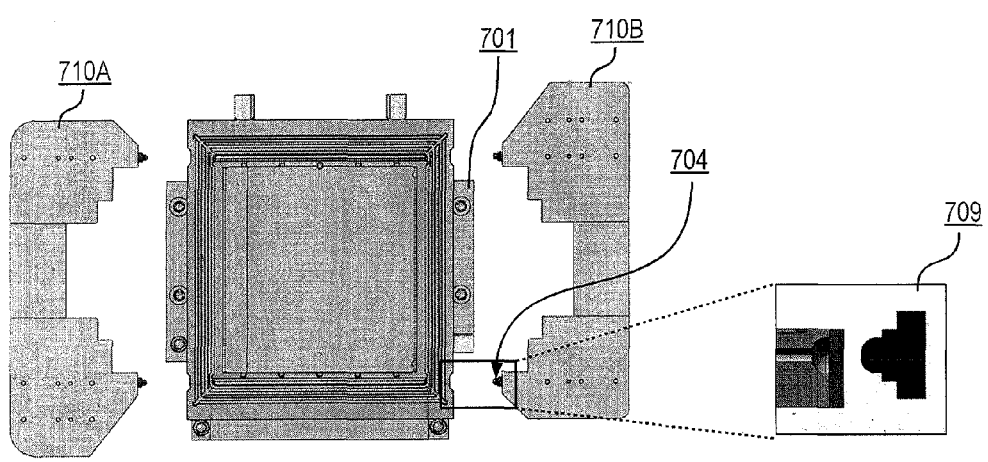

FIGS. 7A, 7B, and 7C illustrate an example embodiment that uses make-and-break seals to load a flow cell, where FIG. 7A illustrates the flow cell prior to a loading operation, FIG. 7B illustrates the flow cell during the loading operation, and FIG. 7C illustrates the flow cell after the loading operation.

FIG. 7A illustrates flow cell 700 being placed or mounted on a chuck 701. For example, flow cell 700 may be placed on chuck 701 by a transfer device such as, for example, a robotic arm, a rail-mounted gantry, or any other suitable precision-controlled device. Source manifold 710A is connected to flexible tubing (not depicted in the figure) that provides fluids (e.g., such as reagents, buffers, and other solutions that may also carry DNA amplicons or other macromolecules) that can flow through suitable channels in the manifold. The fluids are to be dispensed into flow cell 700 through a non-permanent (e.g., make-and-break) fluid connection between source manifold 710A and the flow cell, where the fluid connection is to be sealed through two make-and-break seals. Similarly, drain manifold 710B includes fluidic channels that are connected to flexible tubing (not depicted in the figure) for draining any excess and/or displaced fluids from flow cell 700. The fluids are drained from flow cell 700 to drain manifold 710B through a non-permanent (e.g., make-and-break) fluid connection that is sealed by two make-and-break seals, such as seal 704. Inset 705 depicts a cross-sectional view that illustrates seal 704 prior to being engaged with flow cell 700. It is noted that flow cell 700 is placed on chuck 701, but is not connected to any permanent tubing.

In FIG. 7B, flow cell 700 is automatically clamped in place, source manifold 710A is engaged to the flow cell for dispensing fluid, and drain manifold 710B is also engaged with the flow cell for draining any excess or displaced fluids. Inset 707 depicts a cross-sectional view that illustrates make-and-break seal 704 being engaged with the corresponding outlet port of flow cell 700. After the source and drain manifolds are engaged, the fluids are pumped into the channels of source manifold 710A from one or more reservoirs or other fluidic containers (not shown in the figure). The pumping of fluids is performed by devices and mechanisms that are typically used in a pressurized fluidic system including, but not limited to, pumps, valves, motors, and the like. Since the make-and-break seals provide a sealed (but not permanent) connection between source manifold 710A and the inlet ports of flow cell 700, the fluids flow under the pressure into the inlet manifold of the flow cell and then into the flow cell reaction chamber. Any excess or displaced fluids drain into drain manifold 710B through fluidic connections sealed by the drain manifold make-and-break seals (e.g., seal 704).

In FIG. 7C, flow cell 700 is loaded with the desired fluid(s) and source manifold 710A and drain manifold 710B are disengaged from the flow cell. Inset 709 depicts a cross-sectional view that illustrates make-and-break seal 704 being disengaged from the corresponding outlet port of flow cell 700. It is noted that after the source and drain manifolds are disengaged, flow cell 700 is not connected to any permanent tubing and thus can be moved for further processing to another loading station, e.g., another (possibly physically separate device, or to a different apparatus altogether. For example, flow cell 700 may be moved away from chuck 701 by a transfer device such as, for example, a robotic arm, a rail-mounted gantry, or any other suitable precision-controlled device.

Figure 8:
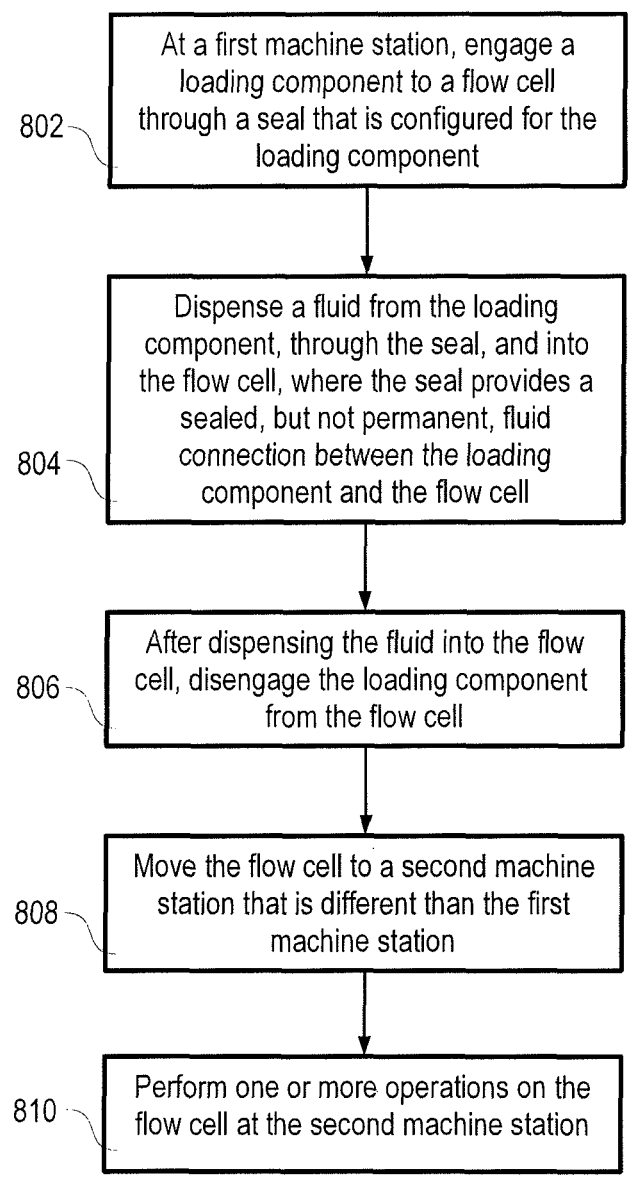
FIG. 8 illustrates a method of using flow cells with make-and-break seals in accordance with an example embodiment.

FIG. 8 illustrates an example method of using flow cells with make-and-break seals. In one embodiment the method of FIG. 8 may be used on a flow cell with a single reaction chamber, such as the flow cell illustrated in FIGS. 5A-5E. In this embodiment, the flow cell comprises a coverslip, a substrate disposed below the coverslip to form the reaction chamber, and an inlet manifold, where the substrate is disposed partially on top of the inlet manifold such that an inlet slit is formed along the edge of the substrate. In another embodiment the method of FIG. 8 may be used on a flow cell with multiple flow regions, such as the flow cells illustrated in FIGS. 1-4. In various embodiments, the method of FIG. 8 may be performed by a sequencing apparatus that comprises a transfer device, which is configured and operable to transport a flow cell between different stations on the same apparatus or a different apparatus, as well as other devices and components that are typical of a sequencing apparatus, including, but not limited to, a reaction sub-system (configured and operable to load fluids and reagents at multiple stations) and an imaging sub-system (configured and operable to image, or otherwise extract information about, the biochemical experiments conducted in the flow cell). In some embodiments, the method of FIG. 8 may be performed by a loader device that is designed specifically for loading a particular type of fluid into a flow cell. For example, in some embodiments a loader device may be configured to load a flow cell with a specific type of macromolecules (e.g., such as DNBs or balled clumps of DNA strings), where the nature of such macromolecules requires specific pressure (e.g., in order to prevent macromolecule shearing), specific temperature, and specific loading times in order to achieve efficient loading.

In step 802, a loading component is engaged to a flow cell at a first station. The loading component may comprise a source manifold (as described heretofore) or any other suitable components such as, for example, injectors, rigid pipes, loading tips, etc. The loading component is fitted, configured, or otherwise aligned, with a make-and-break seal that provides a sealed, but not permanent, fluid connection between the loading component and the flow cell. (As used herein, "fluid connection" refers to a conduit through which a fluid can flow.) For example, in some embodiments one end of the make-and-break seal (or an assembly therefor) may be permanently attached to the loading component; in other embodiments one end of the make-and-break seal (or an assembly therefor) may be permanently attached to the flow cell; and in yet other embodiments, the make-and-break seal may comprise seals on both ends and may be mounted on a mechanism (e.g., such as a precision-controlled device), so that when engaged the make-and-break seal can be aligned with high precision to corresponding openings in the loading component and the flow cell, and when disengaged the make-and-break seal is permanently disconnected from both the loading component and the flow cell. In various embodiments, the engagement of the loading component to the flow cell may be performed by various actuators, motors, and/or other devices that are suitable for effectuating motion; such actuators, motors, and devices are generally known to the skilled persons in the electro-mechanical arts.

In some embodiments, in addition to engaging a loading component to a flow cell through a make-and-break seal, a drain component may also be engaged to the flow cell through a second make-and-break seal, where the second make-and-break seal also provides a sealed, but not permanent, fluid connection between the flow cell and the drain component. In such embodiment, the drain component may comprise a drain manifold (as described heretofore) or any other suitable components such as, for example, pipes, drain tips, funnels, etc. Further, similarly to the make-and-break seal for the loading component, in some embodiments one end of the drain make-and-break seal (or an assembly therefor) may be permanently attached to the drain component. In other embodiments, one end of the drain make-and-break seal (or an assembly therefor) may be permanently attached to the flow cell. In yet other embodiments, the drain make-and-break seal may comprise seals on both ends and may be mounted on a mechanism (e.g., such as a precision-controlled device), so that when engaged the make-and-break seal can be aligned with high precision to corresponding openings in the drain component and the flow cell, and when disengaged the make-and-break seal is permanently disconnected from both the drain component and the flow cell.

In step 804, a fluid is dispensed from the loading component, through the make-and-break seal, and into the flow cell. During this loading operation, the make-and-break seal provides a sealed, but not permanent, fluid connection between the loading component and the flow cell. In some embodiments, the fluid is dispensed under pressure and the make-and-break seal ensures that there are no leaks at the interface between the loading component and the flow cell; under such pressure, the fluid is dispensed through the flow cell ports and into the reaction chamber(s) of the cell. In various embodiments, the fluid may be a mixture or solution including, but not limited to, macromolecules, DNA amplicons, molecules of DNA fragments, buffers, and various reagents such as, for example, reagents used in cPAL sequencing (described hereinafter).

In embodiments that engage a drain component to the flow cell by using drain make-and-break seal(s), the dispensing of the fluid during the loading operation may cause at least a portion of the fluid to flow through a sealed (but not permanent) fluid connection from the flow cell outlet manifold through the drain make-and-break seal(s) and into the drain component.

After the fluid is dispensed into the flow cell, in step 806 the loading component is disengaged from the flow cell. In embodiments in which the make-and-break seal is permanently attached to the loading component or is not permanently attached to any of the loading component or the flow cell, the make-and-break seal is also disengaged from the flow cell. In embodiments that engage a drain component to the flow cell by using drain make-and-break seal(s), the drain component is also disengaged from the flow cell. If the drain make-and-break seal is permanently attached to the loading component or is not permanently attached to any of the loading component or the flow cell, the drain make-and-break seal is also disengaged from the flow cell. Thus, at this point the loading operation is complete (e.g., the flow cell is loaded with the desired fluid), and the flow cell is disconnected and disengaged from any and all loading/unloading components, tubing, pipes, valves, and rigid or flexible connections that were used to load the flow cell with fluids.

In step 808, the flow cell is moved to a second station that is different than the station at which the loading operation was performed. The flow cell may be moved or transported by any suitable transport device; examples of such devices include, but are not limited to, a lab robot, a robotic arm, a rail-mounted gantry, and/or any other suitable precision-controlled device that can be configured to pick up and transport flow cells. In some embodiments, the second station may be located at a physically separate location in the same apparatus (e.g., such as a sequencing apparatus). In other embodiments, the loading station may be part of one apparatus, and the second station (to which the flow cell is moved after loading) may be part of a different apparatus. Examples of stations to which a flow cell can be moved include, without limitation, a (different) loading station, an incubator hotel (configured to host flow cell during incubation cycles), a storage rack, an imaging station, and any apparatus location that is configured to process a flow cell. More generally, the technique of using make-and-break seals described herein allows a flow cell to be moved to any desired location for any desired processing because the flow cell is not permanently attached to any tubing or any other fluidic fixtures and is therefore not stationary between the various operation cycles.

In step 810, one or more operations are performed on the flow cell at the second station to which the flow cell was moved. For example, the second station may be an imaging station that is configured to use an imaging device to record fluorescent signals emitted from the biochemical experiments conducted in the flow cell. In another example, at the second station a second loading component may be engaged to the flow cell through a make-and-break seal that is configured for the second loading component. Then, a different and/or additional fluid may be dispensed from the second loading component, through the make-and-break seal, and into the flow cell, where the seal provides a sealed, but not permanent, fluid connection between the second loading component and the flow cell. After dispensing the different/additional fluid into the flow cell, the second loading component is disengaged from the flow cell. The flow cell can then be moved, or otherwise transported, to a third loading station that is different than the second station. This ability to move the flow cell among different loading stations may be beneficial in embodiments in which multiple different types of fluid need to be loaded into the flow cell in several sequential cycles, because each loading station may be configured for loading a specific type of fluid(s) thereby avoiding the need to flush the tubing after each cycle.

Types of Fluids

The flow cell embodiments described herein can be used with various types of fluids for heterogeneous reactions that take place on the surface of a substrate in a reaction chamber. Examples of such types of fluids are any fluids that need to be dispensed in uniform dosage on a surface for various purposes that include, but are not limited to, sequencing DNA, synthesizing DNA molecules, synthesizing various oligomers and polymers, and any processing that involves the sequential introduction of fluids (e.g., such as active reagent, cleaning reagent, another active reagent, etc.) into the reaction chamber of a flow cell.

Flow Cell Construction

In some embodiments, one or more layers (e.g., such as a reflective layer and/or a fluorescence enhancement layer) may be disposed on a flow cell substrate, such as substrate 504 in FIG. 5C and substrate 230 in FIG. 2C. For example, the substrate may itself be composed of a reflective material (e.g., such as a metal or a Bragg reflector), or it may be a base of substantially any coatable material that provides a solid support on which a fluorescent reflective layer can be disposed. The fluorescent reflective layer of the substrate may be made up of a thin, transparent, dielectric layer or a stack of thin, transparent, dielectric layers, where such dielectric materials include, but are not limited to, $SiO_2$, $TiO_2$, $Ta_2O_5$, $HfO_2$, $ZrO_2$, $MgO$, $Si_3N_4$, $MgF_2$ and $YF_3$.

In some embodiments, attachment sites may be defined by depressions or raised areas in the fluorescence reflective layer of the flow cell substrate, such as substrate 504 in FIG. 5C and substrate 230 in FIG. 2C. In such embodiments, the size (e.g., length/width or diameter) of the attachment sites may be between 30-1000 nm in width, and in a preferred aspect the attachment sites may be 200-500 nm in width, even more preferably approximately 300 nm in width. In another specific aspect, the attachment sites may be separated by a distance of between 0.5 to 10 μm, preferably between 1-3 μm. Nucleic acid macromolecules can be placed on the attachment sites to form an array. The nucleic acid molecules are preferably disposed within each discrete attachment site in a manner that provides very high density and discrete analysis of the individual nucleic acid constructs. In specific aspects, each attachment site of a flow cell is disposed to accept a single macromolecule and, when macromolecules are placed in the flow cell, at least a majority of the attachment sites hold single macromolecules. In some embodiments the distance between the target nucleic acid molecules, which have attached to the attachments sites on a flow cell substrate, provides discrete analysis (e.g., such as sequence determination) for at least 30% of the nucleic acid constructs, preferably at least 50% of the nucleic acid constructs, more preferably at least 70% of the nucleic acid constructs, and optimally at least 90% of the nucleic acid constructs.

The substrate layer or layers of the flow cells described herein can be constructed using various multi-layer coating technologies. The optimization of the multilayer coating design can be done by applying one or more of the well-known techniques in the art. For example, a substrate base may be coated by any one of the following methods: thermal and/or electron beam vapor deposition, replication, transfer, film deposition, by processes of the CVD type (e.g., like LPCVD, PECVD etc.) or of the PVD type such as sputtering, e.g., DC magnetron sputtering. Ion-assisted deposition processes can be used as well as the sol-gel process. Substrate layers may be optionally transferred onto the substrate base by bonding or molecular adhesion.

In embodiments where depressions or raised areas in a fluorescence layer of the flow cell substrate are desirable, multi-layer deposition on a reflective substrate base (or on a reflective layer thereof) may be used to produce the desired structures. For example, a multilayer dielectric fluorescence layer can be designed using a layer of a material with a higher refractive index e.g., $Si_3N_4$ (having a refractive index of n=2.0), disposed on a dielectric material with a lower optical refractive index such as $SiO_2$ (n=1.48). Other coating materials, including multilayer coatings comprising more than two materials, can be used as well. In some embodiments, various structures may be constructed in the fluorescence layer in order to improve the detection of the fluorescence signals emanating from the material dispensed thereon.

Etching can be provided by multiple available techniques, such as the damascene technique, whereby openings are selectively etched into a dielectric layer. Generally, a photoresist material is layered onto the dielectric layer and a pattern of openings outlined in the photoresist layer using lithographic techniques. An anisotropic etch is then used to form the openings in the dielectric layer. The photoresist material is then removed. Where multiple layers and depths are desired, such a process may require the use of more than one mask layer with varying resistances to the anisotropic etch processes.

Use of Flow Cells in Assays

The flow cell technology described herein provides improved flow cells that may be used as part of an overall system for biological assays. In preferred aspects, the flow cells described herein may be used for polynucleotide analysis including, but not limited to, expression and transcriptome analysis using nucleic acid microarrays, PCR and other polynucleotide amplification reactions, SNP analysis, proteome analysis, and the like, and particularly nucleic acid sequence determination.

In some embodiments, the flow cells described herein may be adapted so as to be suitable for use in performing replication and/or amplification (e.g., circle dependent replication, circle dependent amplification, or polymerase chain reaction amplification) on samples attached to the flow cell substrates. In such embodiments, the flow cells may have an opening to allow the addition of further reagents. This opening must be designed so that it is transitory and the flow of any new liquids is very tightly controlled to prevent any leakage from the flow cell and to prevent contamination of the flow cell upon addition of any new reagents. For example, make-and-break seals as described herein may be used in conjunction with such opening to seal the flow of desired liquids.

In certain embodiments, for example those envisaged for use with PCR or other reactions in which tightly controlled temperature regulation is required, the flow cells described herein may be equipped with temperature control means to allow for rapid heating and cooling of the sample and PCR mix (e.g., such thermal cycling devices). For example, a flow cell may be provided with an electrical heating element or a Peltier device. The flow cell may also be adapted (e.g., by provision of cooling means) to provide for improved air cooling. Temperature control in the range 3°-105° C. is likely to be sufficient for most applications.

Sequence Determination

The flow cells described herein may be used for a variety of biochemical analyses. One example of such analysis is sequence determination of target nucleic acids of unknown sequence. In various embodiments, a variety of sequencing methodologies may be used to determine a sequence of the nucleic acid macromolecules using the flow cells described herein, including, but not limited to: hybridization methods; sequencing-by-synthesis methods; and ligation-based methods.

In some embodiments, the flow cells described herein may be used for DNA sequencing of whole human genomes. Commercial viability of human genome sequencing services depends in part on the ability to sequence DNA rapidly and accurately. Thus, biochemical array chips in flow cells can be used for DNA sequencing, can support large numbers of parallel DNA experiments, and can facilitate rapid and accurate genomic data acquisition. In at least some DNA sequencing embodiments, biochemical experiments are performed on flow cell chips by washing reagents over them according to precise protocols that specify chemical compounds and mixtures to be used, concentration, temperature, incubation time, and other parameters appropriate to a particular type of experiment.

Data extraction typically requires two types of image data: bright field images to demarcate the positions of all DNBs in the array; and sets of fluorescence images acquired during each sequencing cycle. The data extraction software identifies all objects with the brightfield images, then for each such object, computes an average fluorescence value for each sequencing cycle. For any given cycle, there are four data-points, corresponding to the four images taken at different wavelengths to query whether that base is an A, G, C or T. These raw base-calls are consolidated, yielding a (possibly discontinuous) sequencing read for each DNB. These sequencing reads may then be matched against a reference genome by using various techniques and algorithms that can be performed on one or more computer systems.

In some embodiments, sequencing of DNA samples (e.g., such as samples representing whole human genomes) may be performed by a sequencing system. An example of a sequencing system is illustrated in FIG. 9.

Figure 9:
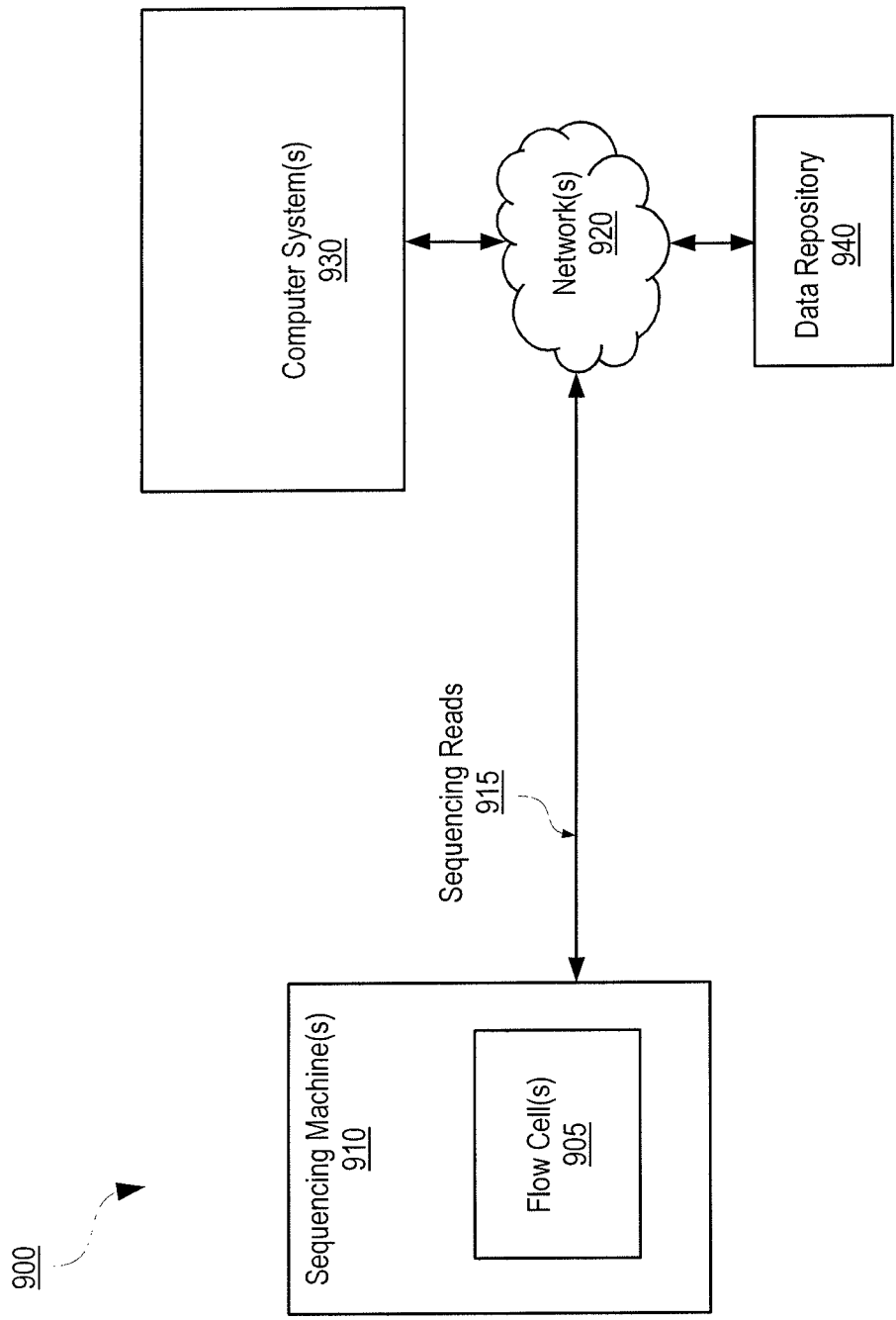
FIG. 9 illustrates an example sequencing system.

In FIG. 9, sequencing system 900 includes multiple subsystems such as, for example, one or more sequencing apparatus 910, one or more computer systems 930, and data repository 940. The various subsystems may be communicatively connected over one or more networks 920, which may include packet-switching or other types of network infrastructure devices (e.g., routers, switches, etc.) that are configured to facilitate information exchange between remote systems.

Sequencing apparatus 910 may itself comprise one or more subsystems such as, for example, a reaction subsystem (e.g., configured to supply reagents, buffers, and other fluids to one or more flow cells 905), an imaging subsystem (e.g., configured to perform image acquisition from the experiments conducted in flow cells 905), and a computer subsystem (e.g., comprising one or more computing devices configured to control the operation of the sequencing apparatus). Sequencing 910 is configured and operable to load target nucleic acids (e.g., such as macromolecules, amplicons, and/or any other types of DNA fragments) into flow cells 905, and to perform sequencing on the target nucleic acids. The sequencing of the target nucleic acids results in reads 915 that may be transmitted to computer system(s) 930 (e.g., for processing) and/or to data repository 940 (e.g., for persistent storage).

Data repository 940 may be implemented on one or more storage devices (e.g., hard-disk drives, optical disks, solid-state drives, etc.) that may be interconnected in a suitable manner such as, for example, a grid, a storage cluster, a storage area network (SAN), and/or a network attached storage (NAS). In various embodiments and implementations, a data repository may be implemented on the storage devices as one or more file systems that store information as files, as one or more databases that store information in data records, and/or as any other suitable storage organization.

Computer system(s) 930 may include one or more computing devices that comprise general purpose processors (e.g., Central Processing Units, or CPUs), memory, and logic which along with configuration data or software can perform various data-processing and/or control functionalities. In some aspects, computer system 930 may be a single computing device. In other aspects, computer system 930 may comprise multiple computing devices that may be communicatively and/or operatively interconnected in a grid, in a cluster, or in a cloud computing operating environment; such multiple computing devices may be configured in different form factors such as computing nodes, blades, or any other suitable hardware configuration.

Figure 10:
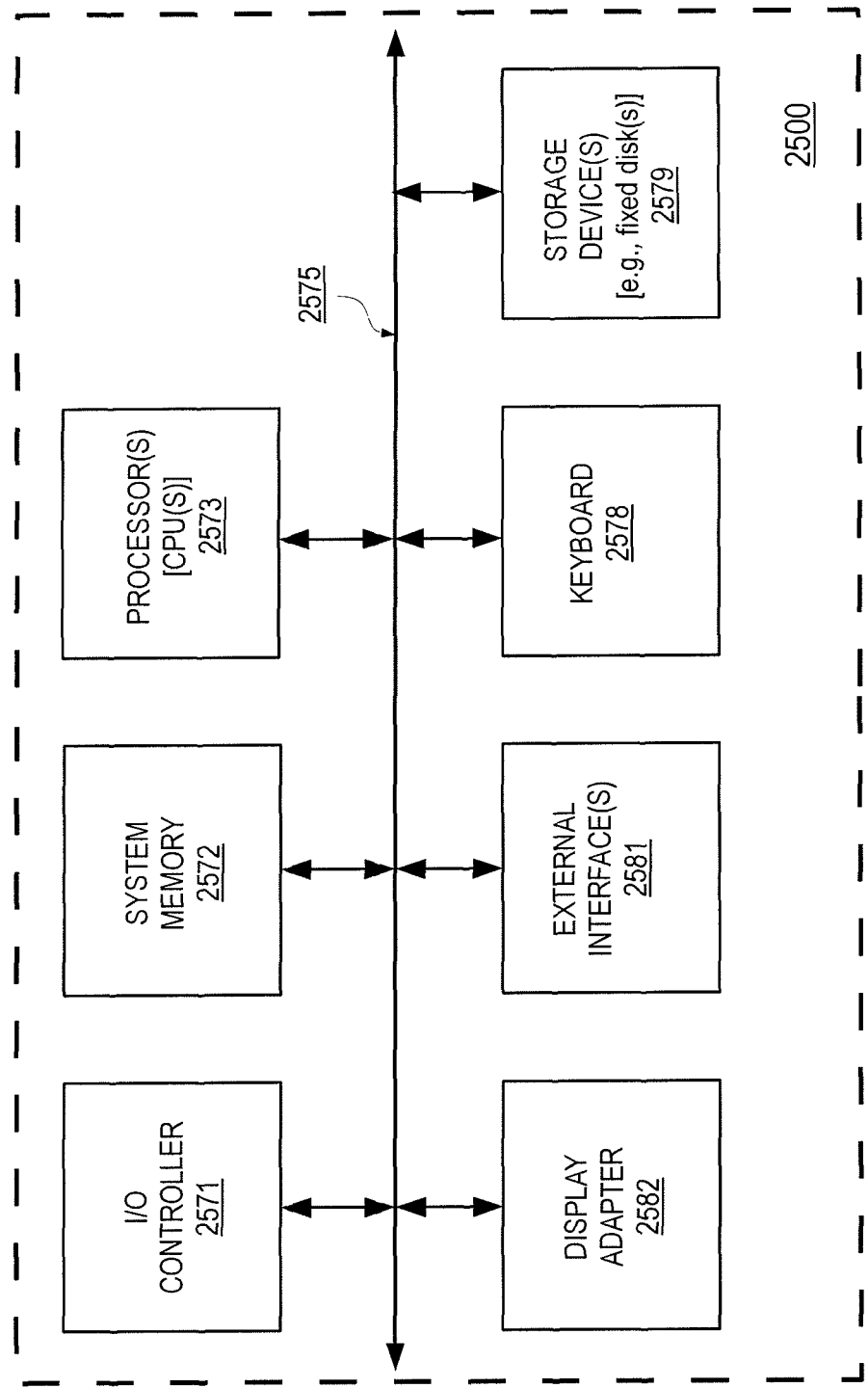
FIG. 10 illustrates an example computing device that can be used in, or in conjunction with, a sequencing system.

FIG. 10 is a block diagram of an example computing device 2500 that can be configured to execute instructions for performing various data-processing and/or control functionalities as part of sequencing apparatus(s) 910 and/or computer system(s) 930.

In FIG. 10, computing device 2500 comprises several components that are interconnected directly or indirectly via one or more system buses such as bus 2575. Such components include, but are not limited to, keyboard 2578, persistent storage device(s) 2579 (e.g., such as fixed disks, solid-state disks, optical disks, and the like), display adapter 2582 and a suitable display device attachable thereto. Peripherals and input/output (I/O) devices, which couple to I/O controller 2571, can be connected to computing device 2500 by any number of means known in the art including, but not limited to, one or more serial ports, one or more parallel ports, and one or more universal serial buses (USBs). External interface(s) 2581 (which may include a network interface card and/or serial ports) can be used to connect computing device 2500 to a network (e.g., such as the Internet or a local area network (LAN)). External interface(s) 2581 may also include a number of input interfaces that can receive information from various external devices such as a sequencing and/or components thereof. The interconnection via system bus 2575 allows one or more CPUs 2573 to communicate with each connected component and to execute (and control the execution of) instructions from system memory 2572 or from storage device(s) 2579, as well as the exchange of information between various components. System memory 2572 (e.g., such Random Access Memory "RAM") and/or storage device(s) 2579 may be embodied as one or more computer-readable non-transitory storage media that store the sequences of instructions executed by central processor(s) 2573 as well as other data. Such computer-readable non-transitory storage media include, but is not limited to, read-only memory (ROM), an electro-magnetic medium (e.g., such as a hard disk drive, solid-state drive, thumb drive, or floppy disk), an optical medium such as a compact disk (CD) or digital versatile disk (DVD), flash memory, and the like. Various data values and other structured or unstructured information can be output from one component or subsystem to another component or subsystem, can be output to a user via display adapter 2582 and a suitable display device coupled thereto, can be sent through external interface(s) 2581 over a network to a remote data repository, or can be stored on storage device(s) 2579.

It should be understood that any of the methods and functionalities performed by computing device 2500 can be implemented in the form of logic using hardware and/or computer software in a modular or integrated manner. As used herein, "logic" refers to a set of instructions which, when executed by one or more processors (e.g., CPUs) of one or more computing devices, are operable to perform one or more functionalities and/or return data in the form of one or more results and/or data that is used by other logic elements. In various embodiments and implementations, any given logic may be implemented as one or more software components that are executable by one or more processors (e.g., CPUs), as one or more hardware components such as Application-Specific Integrated Circuits (ASICs) and/or Field-Programmable Gate Arrays (FPGAs), or as any combination of one or more software components and one or more hardware components. During execution, the instructions of any particular logic may be embodied as one or more computer processes, threads, fibers, and any other suitable run-time entities that can be instantiated on the hardware of one or more computing devices and can be allocated computing resources that may include, without limitation, memory, CPU time, storage space, and network bandwidth.

Single-Cell Multi-Genome Sequencing

In various embodiments, the flow cells described herein can also be used for multi-genome sequencing. In some embodiments, a flow cell includes a single reaction chamber such as, for example, the embodiment illustrated in FIGS. 5A-E. This allows a mixture of target nucleic acid macromolecules (e.g., such as DNBs) from multiple libraries that represent multiple (e.g., human) genomes to be initially dispensed into the flow cell and, after the target macromolecules have attached to the sites on the flow cell chip, various reagents and buffers can be dispensed into the flow cell chamber during the various cycles of sequencing. In other embodiments, a flow cell includes multiple reaction chambers in multiple, separate regions in the flow cell such as, for example, the embodiment illustrated in FIGS. 1-4. In this embodiment, target nucleic acid macromolecules (e.g., such as DNBs) from multiple libraries that represent multiple (e.g., human) genomes can be respectively dispensed into multiple separate flow regions on the flow cell during an initial attachment step. Once the target macromolecules have attached to the sites on the flow cell chip, reagents and buffers are washed over all flow regions of the cell at the same time.

When a chip (or set of chips) large enough to support multiple genomes worth of target macromolecules is contained in a single flow cell, a mechanism may be needed to keep track of which target macromolecules are associated with which genome. One technique for performing such tracking is to use fluorescent tags on the target macromolecules. Fluorescently-tagged target macromolecules from multiple genomes can then be loaded into a single flow cell (such as the single-chamber and multiple-chamber flow cells described herein), and can be efficiently sequenced by using high-throughput sequencing apparatus.

For example, in one embodiment based on the cPAL sequencing technique, a flow cell with a single reaction chamber may be loaded with a mixture containing multiple libraries of DNBs that are derived from the DNA samples of multiple individuals, where the DNBs of each separate individual are labeled with a separate barcode (e.g., a tag) that comprises a short sequence of DNA bases that uniquely identifies the DNBs of that individual. For instance, a library of DNBs derived from a DNA sample of John Doe may be mixed with a library of DNBs derived from a DNA sample from Jane Roe, and then the mixture of the two libraries may be loaded (and sequenced) in the same reaction chamber of a flow cell. In another embodiment, a flow cell having multiple flow regions may be loaded with multiple libraries of DNBs such that the DNBs for each separate individual are directed to a separate region of the flow cell. For instance, DNBs containing DNA from Joe Smith may be loaded (and sequenced) in one flow region of the flow cell, while DNBs containing DNA from Mary Jones may be simultaneously loaded (and sequenced) in a separate flow region of the same flow cell.

While the present invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the claims and their equivalents that issue from the present application. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

What is claimed is:

1. A flow cell comprising:
a coverslip;
a substrate spaced apart from the coverslip to form a reaction chamber between the coverslip and the substrate, the substrate comprising a first edge, a second edge opposed to the first edge, and an array of attachment sites on the substrate, wherein macromolecules introduced into the flow cell attach to the attachment sites;
an outlet in fluid connection with the reaction chamber at or around the second edge of the substrate, the outlet comprising an outlet port;
an inlet in fluid connection with the reaction chamber at or around the first edge of the substrate, the inlet comprising an inlet port and an inlet manifold, wherein the substrate partially covers the inlet manifold to define a space disposed in the inlet manifold below the substrate; and
a bubble port in fluid communication with said space in the inlet manifold below the substrate,
wherein the inlet manifold, the substrate, and the bubble port are configured such that bubbles trapped in said space are constrained to flow out of the bubble port without entering the reaction chamber, and whereby a fluid entering the flow cell by way of the inlet port and the inlet manifold is confined to flow around the first edge of the substrate and into the reaction chamber such that the fluid is substantially free of bubbles.

2. The flow cell of claim 1 further comprising a housing, wherein the inlet manifold is defined within the housing, and wherein an inlet slit is formed between the first edge of the substrate and a side of the housing that defines the inlet manifold.

3. The flow cell of claim 1 comprising inlet ports at opposite ends of the inlet manifold along an axis that is parallel to the first edge of the substrate.

4. The flow cell of claim 1 further comprising a housing that defines an outlet manifold, wherein an outlet slit is formed between the second edge of the substrate and a side of the housing that defines the outlet manifold, wherein fluid flowing out of the flow cell flows from the reaction chamber around the second edge of the substrate, through the outlet slit, into the outlet manifold and through the outlet port.

5. The flow cell of claim 1 further comprising a housing, wherein:
the outlet comprises an outlet manifold comprising a wall that is configured to receive a plug or a loading tip for introducing a macromolecule into the flow cell; and
the inlet manifold and the outlet manifold are defined within the housing.

6. The flow cell of claim 5 comprising outlet ports at opposite ends of the outlet manifold along an axis that is parallel to the second edge of the substrate.

7. The flow cell of claim 1 wherein the reaction chamber comprises two or more separate flow regions, each flow region comprising a loading port configured to receive a plug or a loading tip for introducing macromolecules into such flow region.

8. The flow cell of claim 1 wherein the inlet port is configured to receive an injector component comprising a make-and-break seal.

9. The flow cell of claim 8 wherein the inlet port is adapted to receive an injector component comprising a make-and-break seal having a shape selected from the group consisting of: a hemispherical shape with an annular cross-section, a conical shape, and a flat shape.

10. An apparatus configured for biological analysis of macromolecules comprising one or more flow cells of claim 1.

11. The apparatus of claim 10 comprising a first station for performing a first operation on the flow cell, a second station for performing a second operation on the flow cell, and a transport device for moving the flow cell from the first station to the second station.

12. The apparatus of claim 10 for sequencing nucleic acids, wherein the macromolecules are nucleic acids.

13. A method of using the apparatus of claim 10, the method comprising performing a first operation on the flow cell, transporting the flow cell to a second, different apparatus, and performing a second operation on the flow cell at the second apparatus.

14. The apparatus of claim 10 wherein the flow cell comprises one or more inlet ports that are configured to receive an injector component comprising a make-and-break seal.

15. The flow cell of claim 1 wherein the inlet slit has dimensions and/or a cross section that prevents bubbles from entering the reaction chamber.

* * * * *